(12) United States Patent
Stoks et al.

(10) Patent No.: US 10,080,866 B2
(45) Date of Patent: Sep. 25, 2018

(54) MEDICAL TUBES AND METHODS OF MANUFACTURE

(75) Inventors: Elmo Benson Stoks, Auckland (NZ); Charles Christopher North, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 878 days.

(21) Appl. No.: 14/123,485

(22) PCT Filed: May 30, 2012

(86) PCT No.: PCT/IB2012/001786
§ 371 (c)(1),
(2), (4) Date: Mar. 28, 2014

(87) PCT Pub. No.: WO2012/164407
PCT Pub. Date: Dec. 6, 2012

(65) Prior Publication Data
US 2014/0202462 A1 Jul. 24, 2014

Related U.S. Application Data

(60) Provisional application No. 61/492,970, filed on Jun. 3, 2011, provisional application No. 61/610,109, filed on Mar. 13, 2012.

(51) Int. Cl.
*A61M 25/00* (2006.01)
*A61M 13/00* (2006.01)
(Continued)

(52) U.S. Cl.
CPC .......... *A61M 25/005* (2013.01); *A61M 13/00* (2013.01); *A61M 16/0875* (2013.01);
(Continued)

(58) Field of Classification Search
CPC .............. A61M 16/08; A61M 16/0875; A61M 16/0883; A61M 16/1095; A61M 25/0012;
(Continued)

(56) References Cited

U.S. PATENT DOCUMENTS 2,516,864 A    8/1950   Gilmore et al.
3,117,596 A *   1/1964   Kahn .................... F16L 11/133
                                                      138/111

(Continued)

FOREIGN PATENT DOCUMENTS

CN        2243015 Y     12/1996
CN        201672170      12/2015
(Continued)

OTHER PUBLICATIONS

Machine translation of DE 102006056781 A1.*
(Continued)

*Primary Examiner* — (Jackie) Tan-Uyen T Ho
*Assistant Examiner* — Joseph D Boecker
(74) *Attorney, Agent, or Firm* — Knobbe, Martens, Olson & Bear, LLP

(57) ABSTRACT

The disclosure relates to medical tubes and methods of manufacturing medical tubes. The tube may be a composite structure made of two or more distinct components that are spirally wound to form an elongate tube. For example, one of the components may be a spirally wound elongate hollow body, and the other component may be an elongate structural component also spirally wound between turns of the spirally wound hollow body The tube need not be made from distinct components, however. For instance, an elongate hollow body formed (e.g., extruded) from a single material may be spirally wound to form an elongate tube. The elongate hollow body itself may in transverse cross-section have a thin wall portion and a relatively thicker or more rigid (Continued)

reinforcement portion. The tubes can be incorporated into a variety of medical circuits or may be employed for other medical uses.

35 Claims, 27 Drawing Sheets

(51) Int. Cl.
*A61M 16/08* (2006.01)
*A61M 39/00* (2006.01)
*A61M 16/10* (2006.01)
*B29C 53/78* (2006.01)
*B29C 53/60* (2006.01)
*A61M 5/44* (2006.01)
*A61M 16/16* (2006.01)

(52) U.S. Cl.
CPC .... *A61M 16/0883* (2014.02); *A61M 16/1095* (2014.02); *A61M 39/00* (2013.01); *B29C 53/60* (2013.01); *B29C 53/785* (2013.01); *A61M 5/44* (2013.01); *A61M 16/0833* (2014.02); *A61M 16/16* (2013.01); *A61M 2205/3368* (2013.01); *A61M 2205/75* (2013.01); *A61M 2207/00* (2013.01); *Y10T 29/49826* (2015.01)

(58) Field of Classification Search
CPC ............ A61M 25/005; A61M 25/0054; A61M 39/00; A61M 2207/00; B29C 53/60; B29C 53/78; B29C 53/785
See application file for complete search history.

(56) References Cited

U.S. PATENT DOCUMENTS

| | | | |
|---|---|---|---|
| 4,160,466 A * | 7/1979 | Jousson | B29C 53/083 138/115 |
| 4,301,200 A | 11/1981 | Langenfeld et al. | |
| 4,428,403 A * | 1/1984 | Lee | A61M 5/44 138/123 |
| 4,531,551 A | 7/1985 | Eichelberger et al. | |
| 5,127,442 A | 7/1992 | Blomqvist | |
| 5,591,292 A * | 1/1997 | Blomqvist | B29C 53/78 156/244.13 |
| 5,630,806 A | 5/1997 | Inagaki et al. | |
| 5,640,951 A | 6/1997 | Huddart et al. | |
| 6,190,480 B1 | 2/2001 | Carlson | |
| 6,347,646 B2 * | 2/2002 | Fukui | 138/121 |
| 6,374,864 B1 * | 4/2002 | Philp | F16L 11/24 138/119 |
| 6,394,145 B1 | 5/2002 | Gessil | |
| 6,540,734 B1 * | 4/2003 | Chiu | A61M 25/1011 604/508 |
| 7,766,050 B2 * | 8/2010 | Patel | A61M 16/08 138/129 |
| 2004/0079371 A1 * | 4/2004 | Gray | A61M 16/08 128/204.17 |
| 2004/0099268 A1 | 5/2004 | Smith et al. | |
| 2004/0244858 A1 | 12/2004 | Jeong | |
| 2005/0059957 A1 * | 3/2005 | Campbell | A61M 25/0043 604/524 |
| 2005/0152733 A1 * | 7/2005 | Patel | A61M 16/08 400/625 |
| 2006/0165829 A1 * | 7/2006 | Smith | A61M 16/08 425/113 |
| 2008/0251073 A1 * | 10/2008 | Jassell | A61M 16/0875 128/204.17 |

FOREIGN PATENT DOCUMENTS

| | | | |
|---|---|---|---|
| DE | 102006056781 A1 * | 6/2008 | ............ B29C 53/78 |
| EP | 0111 248 A2 | 6/1984 | |
| EP | 0232864 B1 | 5/1994 | |
| EP | 0672430 A2 | 9/1995 | |
| EP | 1396277 A2 | 3/2004 | |
| EP | 1535722 A2 | 6/2005 | |
| JP | 59-113392 | 6/1984 | |
| JP | 11-286058 A | 10/1999 | |
| JP | 2001-511507 A | 8/2001 | |
| JP | 2003-139276 A | 5/2003 | |
| JP | 44-022293 U | 2/2010 | |
| WO | WO 2004/024429 A1 | 3/2004 | |
| WO | WO 2008/060046 | 5/2008 | |

OTHER PUBLICATIONS

International Preliminary Report on Patentability; Application No. PCT/IB2012/001786; Filed May 30, 2012.
International Search Report; PCT/IB2012/001786; dated Nov. 21, 2012.

* cited by examiner

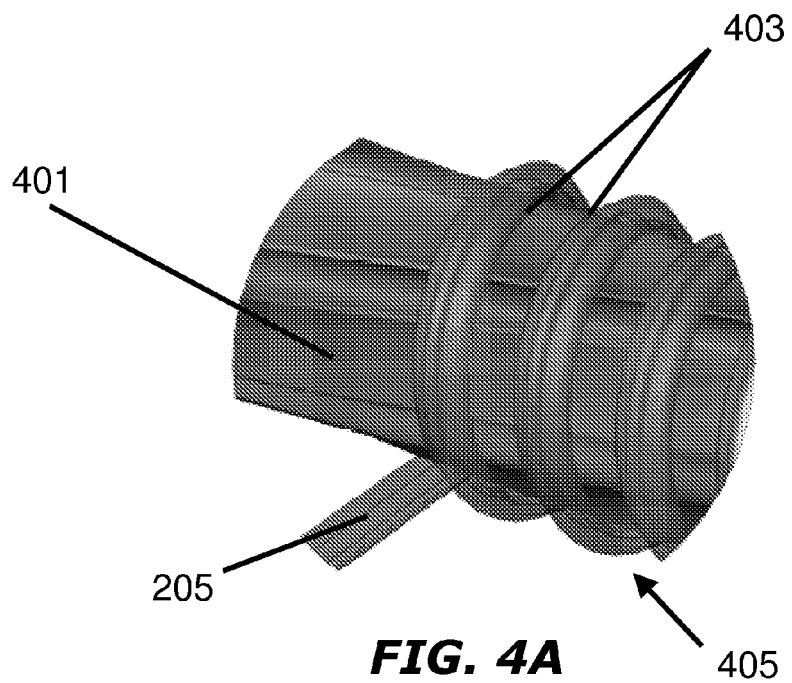
FIG. 4A
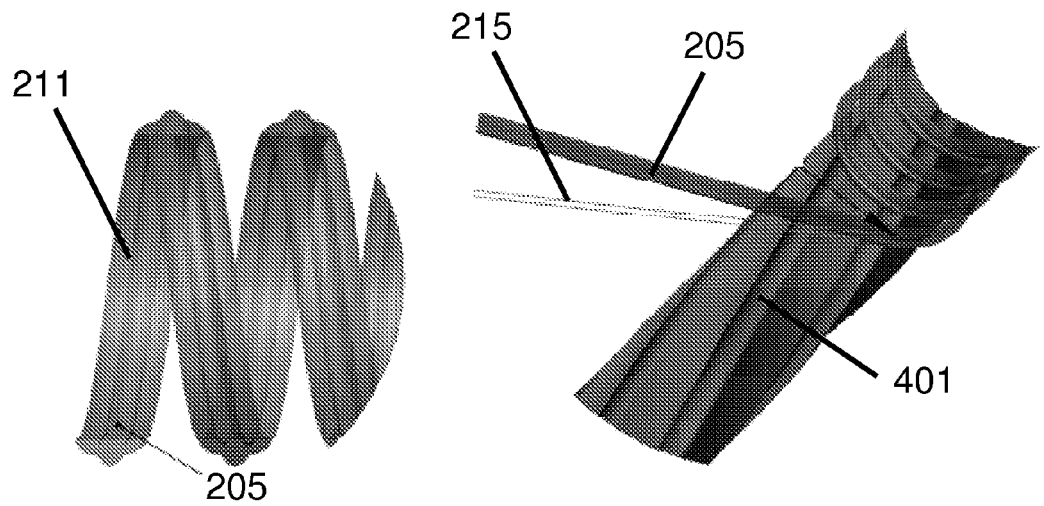
FIG. 4B  FIG. 4C

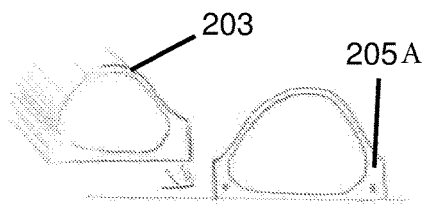
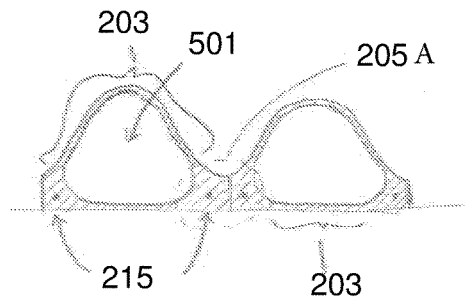
FIG. 5A  FIG. 5B
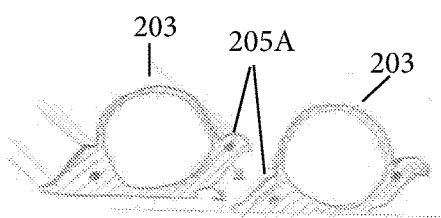
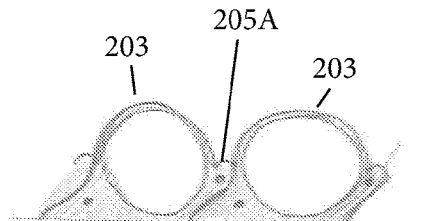
FIG. 5C  FIG. 5D
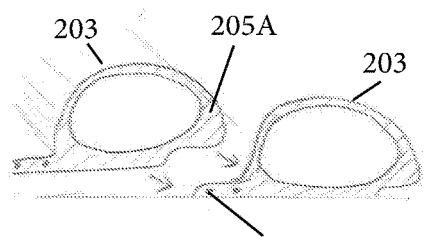
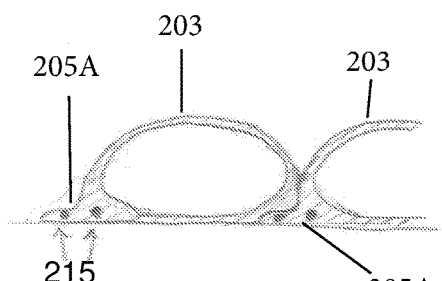
FIG. 5E  FIG. 5F

MEDICAL TUBES AND METHODS OF MANUFACTURE

BACKGROUND

Field

This disclosure relates generally to tubes suitable for medical use, and in particular to tubes for use in medical circuits suitable for providing gases to and/or removing gases from a patient, such as in positive airway pressure (PAP), respirator, anaesthesia, ventilator, and insufflation systems.

Description of the Related Art

In medical circuits, various components transport warm and/or humidified gases to and from patients. For example, in some breathing circuits such as PAP or assisted breathing circuits, gases inhaled by a patient are delivered from a heater-humidifier through an inspiratory tube. As another example, tubes can deliver humidified gas (commonly $CO_2$) into the abdominal cavity in insufflation circuits. This can help prevent "drying out" of the patient's internal organs, and can decrease the amount of time needed for recovery from surgery. Unheated tubing allows significant heat loss to ambient cooling. This cooling may result in unwanted condensation or "rainout" along the length of the tubing transporting warm, humidified air. A need remains for tubing that insulates against heat loss and, for example, allows for improved temperature and/or humidity control in medical circuits.

SUMMARY

Medical tubes and methods of manufacturing medical tubes are disclosed herein in various embodiments. In some embodiments, the tube may be a composite structure made of two or more distinct components that are spirally wound to form an elongate tube. For example, one of the components may be a spirally wound elongate hollow body, and the other component may be an elongate structural component also spirally wound between turns of the spirally wound hollow body In other embodiments, the tube need not be made from distinct components. For instance, an elongate hollow body formed (e.g., extruded) from a single material may be spirally wound to form an elongate tube. The elongate hollow body itself may in transverse cross-section have a thin wall portion and a relatively thicker or more rigid reinforcement portion. The tubes can be incorporated into a variety of medical circuits or may be employed for other medical uses.

In at least one embodiment, a composite tube can comprise a first elongate member comprising a hollow body spirally wound to form at least in part an elongate tube having a longitudinal axis, a lumen extending along the longitudinal axis, and a hollow wall surrounding the lumen. A second elongate member may be spirally wound and joined between adjacent turns of the first elongate member, the second elongate member forming at least a portion of the lumen of the elongate tube. The name "first elongate member" and "second elongate member" do not necessarily connote an order, such as the order in which the components are assembled. As described herein, the first elongate member and the second elongate member can also be portions of a single tube-shaped element.

In various embodiments, the foregoing component has one, some, or all of the following properties, as well as properties described elsewhere in this disclosure.

The first elongate member can be a tube. The first elongate member can form in longitudinal cross-section a plurality of bubbles with a flattened surface at the lumen. Adjacent bubbles can be separated by a gap above the second elongate member, or may not be directly connected to each other. The bubbles can have perforations. The second elongate member can have a longitudinal cross-section that is wider proximal the lumen and narrower at a radial distance from the lumen. Specifically, the second elongate member can have a longitudinal cross-section that is generally triangular, generally T-shaped, or generally Y-shaped. One or more conductive filaments can be embedded or encapsulated in the second elongate member. The one or more conductive filaments can be heating filaments (or more specifically, resistance heating filaments) and/or sensing filaments. The tube can comprise pairs of conductive filaments, such as two or four conductive filaments. Pairs of conductive filaments can be formed into a connecting loop at one end of the composite tube. The one or more conductive filaments can be spaced from the lumen wall. In at least one embodiment, the second elongate member can have a longitudinal cross-section that is generally triangular, generally T-shaped, or generally Y-shaped, and one or more conductive filaments can be embedded or encapsulated in the second elongate member on opposite sides of the triangle, T-shape, or Y-shape.

The foregoing component according to any or all of the preceding embodiments can be incorporated into a medical circuit component, an inspiratory tube, an expiratory tube, a PAP component, an insufflation circuit, an exploratory component, or a surgical component, among other applications.

A method of manufacturing a composite tube is also disclosed. The resulting tube can have one, some, or all of the properties described above or anywhere in this disclosure. In at least one embodiment, the method comprises providing a first elongate member comprising a hollow body and a second elongate member configured to provide structural support for the first elongate member. The second elongate member is spirally wrapped around a mandrel with opposite side edge portions of the second elongate member being spaced apart on adjacent wraps, thereby forming a second-elongate-member spiral. The first elongate member is spirally wrapped around the second-elongate-member spiral, such that portions of the first elongate member overlap adjacent wraps of the second-elongate-member spiral and a portion of the first elongate member is disposed adjacent the mandrel in the space between the wraps of the second-elongate-member spiral, thereby forming a first-elongate-member spiral.

In various embodiments, the foregoing method can comprise one, some, or all of the following. The method can comprise supplying air at a pressure greater than atmospheric pressure to an end of the first elongate member. The method can comprise cooling the second-elongate-member spiral and the first-elongate-member spiral, thereby forming a composite tube having a lumen extending along a longitudinal axis and a hollow space surrounding the lumen. The method can comprise forming the first elongate member. The method can comprise extruding the first elongate member with a first extruder. The method can comprise forming the second elongate member. The method can comprise extruding the second elongate member with a second extruder. The second extruder can be configured to encapsulate one or more conductive filaments in the second elongate member. Forming the second elongate member can comprise embedding conductive filaments in the second elongate member. The conductive filaments can be non-reactive with the second elongate member. The conductive filaments can comprise alloys of aluminum or copper or other conductive materials. The method can comprise forming pairs of conductive filaments into a connecting loop at one end of the composite tube. The first extruder can be distinct from the second extruder.

A medical tube is also disclosed. In at least one embodiment, the tube comprises an elongate hollow body spirally wound to form an elongate tube having a longitudinal axis, a lumen extending along the longitudinal axis, and a hollow wall surrounding the lumen, wherein the elongate hollow body has in transverse cross-section a wall defining at least a portion of the hollow body. The tube can further comprise a reinforcement portion extending along a length of the elongate hollow body being spirally positioned between adjacent turns of the elongate hollow body, wherein the reinforcement portion forms a portion of the lumen of the elongate tube. The reinforcement portion can be relatively thicker or more rigid than the wall of the elongate hollow body.

In various embodiments, the foregoing tube has one, some, or all of the following properties, as well as properties described elsewhere in this disclosure. The reinforcement portion can be formed from the same piece of material as the elongate hollow body. The elongate hollow body in transverse cross-section can comprise two reinforcement portions on opposite sides of the elongate hollow body, wherein spiral winding of the elongate hollow body joins adjacent reinforcement portions to each other such that opposite edges of the reinforcement portions touch on adjacent turns of the elongate hollow body. Opposite side edges of the reinforcement portions can overlap on adjacent turns of the elongate hollow body. The reinforcement portion can be made of a separate piece of material than the elongate hollow body. The hollow body can form in longitudinal cross-section a plurality of bubbles with a flattened surface at the lumen. The bubbles can have perforations. The medical tube can also comprise one or more conductive filaments embedded or encapsulated within the reinforcement portion. The conductive filament can be a heating filament and/or or sensing filament. The medical tube can comprise two conductive filaments, wherein one conductive filament is embedded or encapsulated in each of the reinforcement portions. The medical tube can comprise two conductive filaments positioned on only one side of the elongate hollow body. Pairs of conductive filaments can be formed into a connecting loop at one end of the elongate tube. The one or more filaments can be spaced from the lumen wall.

The foregoing tube according to any or all of the preceding embodiments can be incorporated into a medical circuit component, an inspiratory tube, an expiratory tube, a PAP component, an insufflation circuit, an exploratory component, or a surgical component, among other applications.

A method of manufacturing a medical tube is also disclosed. In at least one embodiment, the method comprises spirally winding an elongate hollow body around a mandrel to form an elongate tube having a longitudinal axis, a lumen extending along the longitudinal axis, and a hollow wall surrounding the lumen, wherein the elongate hollow body has in transverse cross-section a wall defining at least a portion of the hollow body and two reinforcement portions on opposite sides of the elongate body forming a portion of the wall of the lumen, the two reinforcement portions being relatively thicker or more rigid than the wall defining at least a portion of the hollow body. The method can further comprise joining adjacent reinforcement portions to each other such that opposite edges of the reinforcement portions touch on adjacent turns of the elongate hollow body.

In various embodiments, the foregoing method can comprise one, some, or all of the following or any other properties described elsewhere in this disclosure. Joining adjacent reinforcement portions to each other can cause edges of the reinforcement portions to overlap. The method can further comprise supplying air at a pressure greater than atmospheric pressure to an end of the elongate hollow body. The method can further comprise cooling the elongate hollow body to join the adjacent reinforcement portions to each other. The method can further comprise extruding the elongate hollow body. The method can further comprise embedding conductive filaments in the reinforcement portions. The method can further comprise forming pairs of conductive filaments into a connecting loop at one end of the elongate tube.

For purposes of summarizing the invention, certain aspects, advantages and novel features of the invention have been described herein. It is to be understood that not necessarily all such advantages may be achieved in accordance with any particular embodiment of the invention. Thus, the invention may be embodied or carried out in a manner that achieves or optimizes one advantage or group of advantages as taught herein without necessarily achieving other advantages as may be taught or suggested herein.

BRIEF DESCRIPTION OF THE DRAWINGS

Example embodiments that implement the various features of the disclosed systems and methods will now be described with reference to the drawings. The drawings and the associated descriptions are provided to illustrate embodiments and not to limit the scope of the disclosure.

FIG. 4A shows an aspect in a method for forming the composite tube.

FIG. 4B shows a spiral-wound second elongate member.
FIG. 4C shows another aspect in a method for forming the composite tube.

FIGS. 5A-5B shows another example illustrating a single elongate hollow body being spirally wound to form a medical tube.

FIGS. 5C-5F shows examples of other single elongate hollow bodies being spirally wound to form a medical tube.

Figure 1:
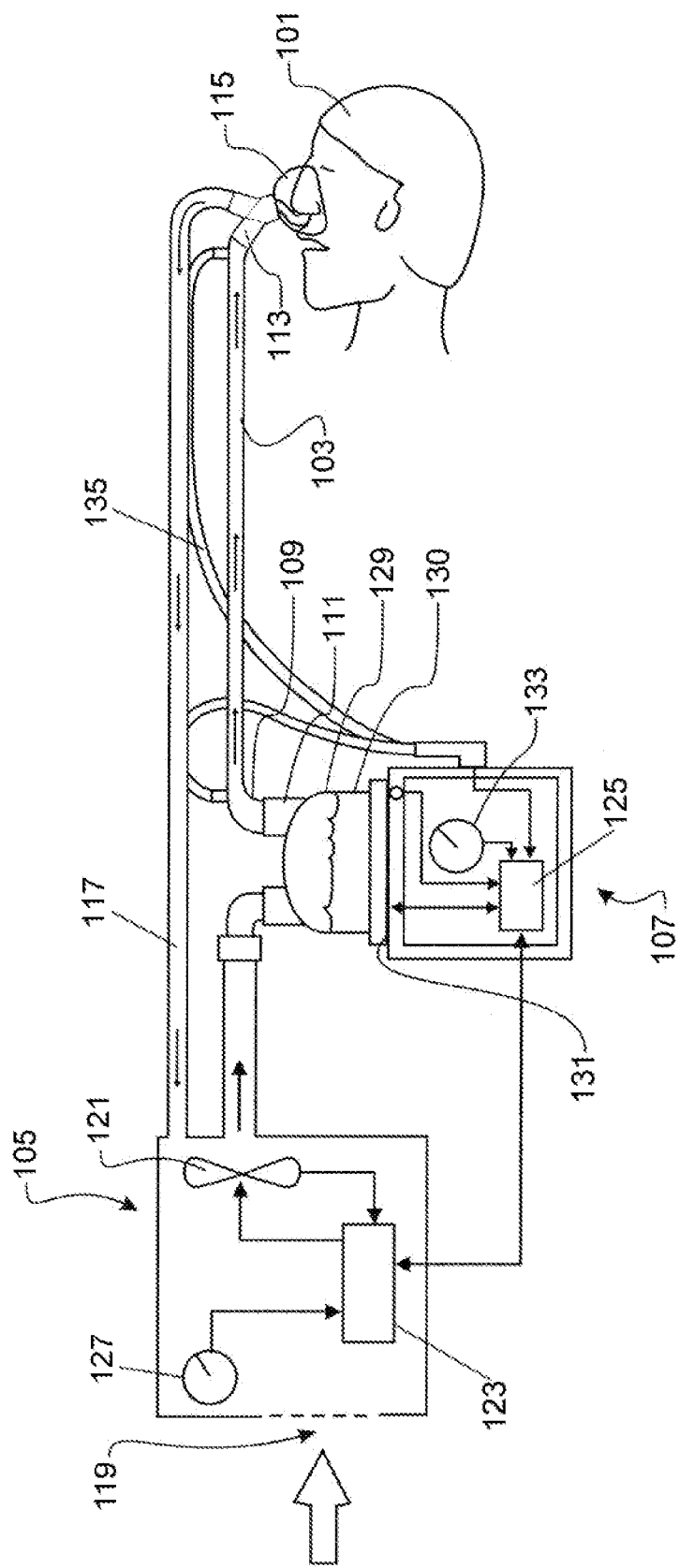
FIG. 1 shows a schematic illustration of a medical circuit incorporating one or more medical tubes.

Throughout the drawings, reference numbers are re-used to indicate correspondence between referenced (or similar) elements. In addition, the first digit of each reference number indicates the figure in which the element first appears.

DETAILED DESCRIPTION

Details regarding several illustrative embodiments for implementing the apparatuses and methods described herein are described below with reference to the figures. The invention is not limited to these described embodiments.
Breathing Circuit Comprising One or More Medical Tubes For a more detailed understanding of the disclosure, reference is first made to FIG. 1, which shows a breathing circuit according to at least one embodiment, which includes one or more medical tubes. Tube is a broad term and is to be given its ordinary and customary meaning to a person of ordinary skill in the art (that is, it is not to be limited to a special or customized meaning) and includes, without limitation, non-cylindrical passageways. Certain embodiments may incorporate a composite tube, which may generally be defined as a tube comprising two or more portions, or, specifically, in some embodiments, two or more components, as described in greater detail below. Such a breathing circuit can be a continuous, variable, or bi-level positive airway pressure (PAP) system or other form of respiratory therapy.

Gases can be transported in the circuit of FIG. 1 as follows. Dry gases pass from a ventilator/blower 105 to a humidifier 107, which humidifies the dry gases. The humidifier 107 connects to the inlet 109 (the end for receiving humidified gases) of the inspiratory tube 103 via a port 111, thereby supplying humidified gases to the inspiratory tube 103. An inspiratory tube is a tube that is configured to deliver breathing gases to a patient, and may be made from a composite tube as described in further detail below. The gases flow through the inspiratory tube 103 to the outlet 113 (the end for expelling humidified gases), and then to the patient 101 through a patient interface 115 connected to the outlet 113.

An expiratory tube 117 also connects to the patient interface 115. An expiratory tube is a tube that is configured to move exhaled humidified gases away from a patient. Here, the expiratory tube 117 returns exhaled humidified gases from the patient interface 115 to the ventilator/blower 105.

In this example, dry gases enter the ventilator/blower 105 through a vent 119. A fan 121 can improve gas flow into the ventilator/blower by drawing air or other gases through vent 119. The fan 121 can be, for instance, a variable speed fan, where an electronic controller 123 controls the fan speed. In particular, the function of the electronic controller 123 can be controlled by an electronic master controller 125 in response to inputs from the master controller 125 and a user-set predetermined required value (preset value) of pressure or fan speed via a dial 127.

The humidifier 107 comprises a humidification chamber 129 containing a volume of water 130 or other suitable humidifying liquid. Preferably, the humidification chamber 129 is removable from the humidifier 107 after use. Removability allows the humidification chamber 129 to be more readily sterilized or disposed. However, the humidification chamber 129 portion of the humidifier 107 can be a unitary construction. The body of the humidification chamber 129 can be formed from a non-conductive glass or plastics material. But the humidification chamber 129 can also include conductive components. For instance, the humidification chamber 129 can include a highly heat-conductive base (for example, an aluminum base) contacting or associated with a heater plate 131 on the humidifier 107.

The humidifier 107 can also include electronic controls. In this example, the humidifier 107 includes an electronic, analog or digital master controller 125. Preferably, the master controller 125 is a microprocessor-based controller executing computer software commands stored in associated memory. In response to the user-set humidity or temperature value input via a user interface 133, for example, and other inputs, the master controller 125 determines when (or to what level) to energize heater plate 131 to heat the water 130 within humidification chamber 129.

Any suitable patient interface 115 can be incorporated. Patient interface is a broad term and is to be given its ordinary and customary meaning to a person of ordinary skill in the art (that is, it is not to be limited to a special or customized meaning) and includes, without limitation, masks (such as tracheal mask, face masks and nasal masks), cannulas, and nasal pillows. A temperature probe 135 can connect to the inspiratory tube 103 near the patient interface 115, or to the patient interface 115. The temperature probe 135 monitors the temperature near or at the patient interface 115. A heating filament (not shown) associated with the temperature probe can be used to adjust the temperature of the patient interface 115 and/or inspiratory tube 103 to raise the temperature of the inspiratory tube 103 and/or patient interface 115 above the saturation temperature, thereby reducing the opportunity for unwanted condensation.

Figure 2A:
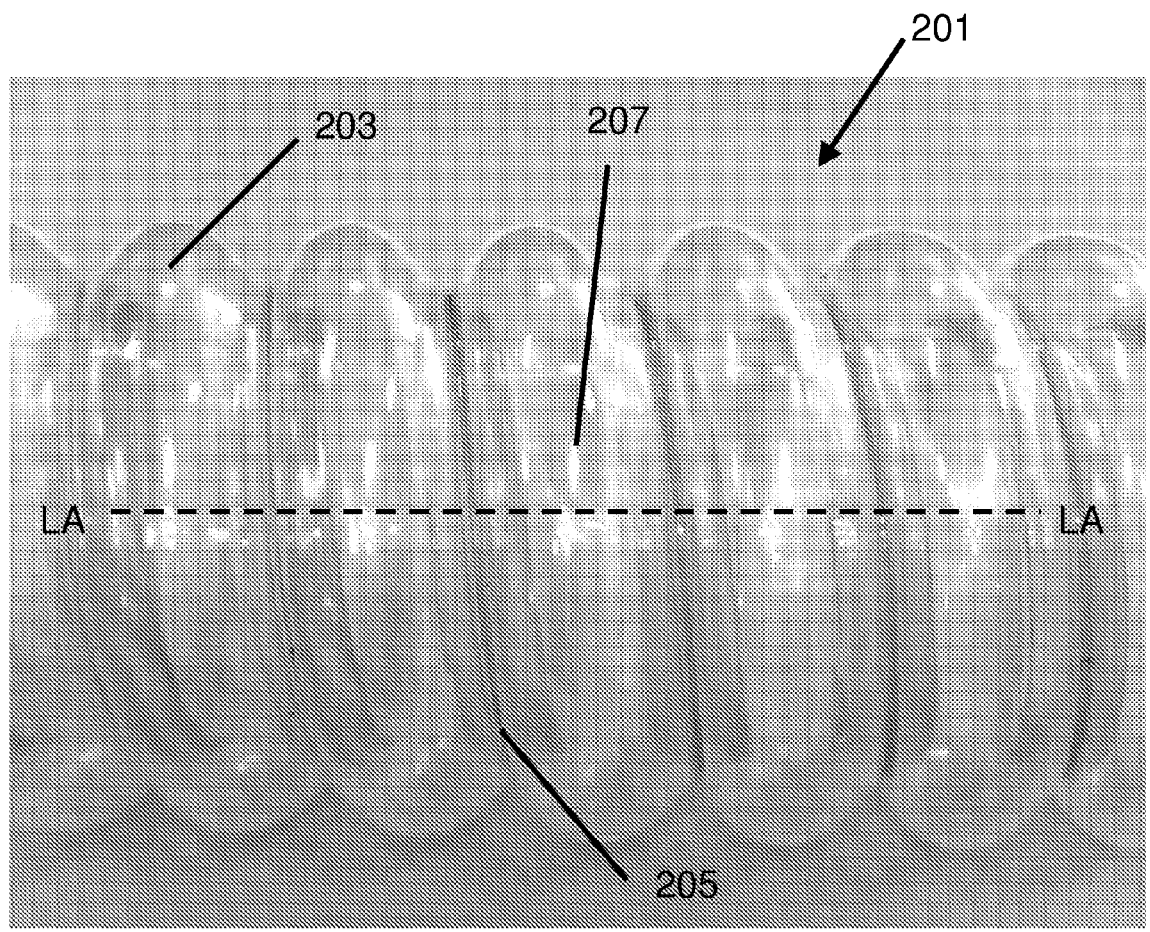
FIG. 2A shows a side-plan view of a section of an example composite tube.

In FIG. 1, exhaled humidified gases are returned from the patient interface 115 to the ventilator/blower 105 via the expiratory tube 117. The expiratory tube 117 can also be a composite tube, as described in greater detail below. However, the expiratory tube 117 can also be a medical tube as previously known in the art. In either case, the expiratory tube 117 can have a temperature probe and/or heating filament, as described above with respect to the inspiratory tube 103, integrated with it to reduce the opportunity for condensation. Furthermore, the expiratory tube 117 need not return exhaled gases to the ventilator/blower 105. Alternatively, exhaled humidified gases can be passed directly to ambient surroundings or to other ancillary equipment, such as an air scrubber/filter (not shown). In certain embodiments, the expiratory tube is omitted altogether.
Composite Tubes FIG. 2A shows a side-plan view of a section of example composite tube 201. In general, the composite tube 201 comprises a first elongate member 203 and a second elongate member 205. Member is a broad term and is to be given its ordinary and customary meaning to a person of ordinary skill in the art (i.e., it is not to be limited to a special or customized meaning) and includes, without limitation, integral portions, integral components, and distinct components. Thus, although FIG. 2A illustrates an embodiment made of two distinct components, it will be appreciated that in other embodiments (such as described in FIGS. 5A-5D below), the first elongate member 203 and second elongate member 205 can also represent regions in a tube formed from a single material. Thus, the first elongate member 203 can represent a hollow portion of a tube, while the second elongate member 205 represents a structural supporting or reinforcement portion of the tube which adds structural support to the hollow portion. The hollow portion and the structural supporting portion can have a spiral configuration, as described herein. The composite tube 201 may be used to form the inspiratory tube 103 and/or the expiratory tube 117 as described above, a coaxial tube as described below, or any other tubes as described elsewhere in this disclosure.

In this example, the first elongate member 203 comprises a hollow body spirally wound to form, at least in part, an elongate tube having a longitudinal axis LA-LA and a lumen 207 extending along the longitudinal axis LA-LA. In at least one embodiment, the first elongate member 203 is a tube. Preferably, the first elongate member 203 is flexible. Furthermore, the first elongate member 203 is preferably transparent or, at least, semi-transparent or semi-opaque. A degree of optical transparency allows a caregiver or user to inspect the lumen 207 for blockage or contaminants or to confirm the presence of moisture. A variety of plastics, including medical grade plastics, are suitable for the body of the first elongate member 203. Examples of suitable materials include Polyolefin elastomers, Polyether block amides, Thermoplastic co-polyester elastomers, EPDM-Polypropylene mixtures, and Thermoplastic polyurethanes.

The hollow body structure of the first elongate member 203 contributes to the insulating properties to the composite tube 201. An insulating tube 201 is desirable because, as explained above, it prevents heat loss. This can allow the tube 201 to deliver gas from a heater-humidifier to a patient while maintaining the gas's conditioned state with minimal energy consumption.

In at least one embodiment, the hollow portion of the first elongate member 203 is filled with a gas. The gas can be air, which is desirable because of its low thermal conductivity ($2.62 \times 10^{-2}$ W/m·K at 300K) and very low cost. A gas that is more viscous than air may also advantageously be used, as higher viscosity reduces convective heat transfer. Thus, gases such as argon ($17.72 \times 10^{-3}$ W/m·K at 300K), krypton ($9.43 \times 10^{-3}$ W/m·K at 300K), and xenon ($5.65 \times 10^{-3}$ W/m·K at 300K) can increase insulating performance. Each of these gases is non-toxic, chemically inert, fire-inhibiting, and commercially available. The hollow portion of the first elongated member 203 can be sealed at both ends of the tube, causing the gas within to be substantially stagnant. Alternatively, the hollow portion can be a secondary pneumatic connection, such as a pressure sample line for conveying pressure feedback from the patient-end of the tube to a controller. The first elongate member 203 can be optionally perforated. For instance, the surface of the first elongate member 203 can be perforated on an outward-facing surface, opposite the lumen 207. In another embodiment, the hollow portion of the first elongate member 203 is filled with a liquid. Examples of liquids can include water or other biocompatible liquids with a high thermal capacity. For instance, nanofluids can be used. An example nanofluid with suitable thermal capacity comprises water and nanoparticles of substances such as aluminum.

The second elongate member 205 is also spirally wound and joined to the first elongate member 203 between adjacent turns of the first elongate member 203. The second elongate member 205 forms at least a portion of the lumen 207 of the elongate tube. The second elongate member 205 acts as structural support for the first elongate member 203.

In at least one embodiment, the second elongate member 205 is wider at the base (proximal the lumen 207) and narrower at the top. For example, the second elongate member can be generally triangular in shape, generally T-shaped, or generally Y-shaped. However, any shape that meets the contours of the corresponding first elongate member 203 is suitable.

Preferably, the second elongate member 205 is flexible, to facilitate bending of the tube. Desirably; the second elongate member 205 is less flexible than the first elongate member 203. This improves the ability of the second elongate member 205 to structurally support the first elongate member 203. For example, the modulus of the second elongate member 205 is preferably 30-50 MPa (or about 30-50 MPa). The modulus of the first elongate member 203 is less than the modulus of the second elongate member 205. The second elongate member 205 can be solid or mostly solid. In addition, the second elongate member 205 can encapsulate or house conductive material, such as filaments, and specifically heating filaments or sensors (not shown). Heating filaments can minimize the cold surfaces onto which condensate from moisture-laden air can form. Heating filaments can also be used to alter the temperature profile of gases in the lumen 207 of composite tube 201. A variety of polymers and plastics, including medical grade plastics, are suitable for the body of the second elongate member 205. Examples of suitable materials include Polyolefin elastomers, Polyether block amides, Thermoplastic co-polyester elastomers, EPDM-Polypropylene mixtures and Thermoplastic polyurethanes. In certain embodiments, the first elongate member 203 and the second elongate member 205 may be made from the same material. The second elongate member 205 may also be made of a different color material from the first elongate member 203, and may be transparent, translucent or opaque. For example, in one embodiment the first elongate member 203 may be made from a clear plastic, and the second elongate member 205 may be made from an opaque blue (or other color) plastic.

This spirally-wound structure comprising a flexible, hollow body and an integral support can provide crush resistance, while leaving the tube wall flexible enough to permit short-radius bends without kinking, occluding or collapsing. Preferably, the tube can be bent around a 25 mm diameter metal cylinder without kinking, occluding, or collapsing, as defined in the test for increase in flow resistance with bending according to ISO 5367:2000(E). This structure also can provide a smooth lumen 207 surface (tube bore), which helps keep the tube free from deposits and improves gas flow. The hollow body has been found to improve the insulating properties of a tube, while allowing the tube to remain light weight.

As explained above, the composite tube 201 can be used as an expiratory tube and/or an inspiratory tube in a breathing circuit, or a portion of a breathing circuit. Preferably, the composite tube 201 is used at least as an inspiratory tube.

Figure 2B:
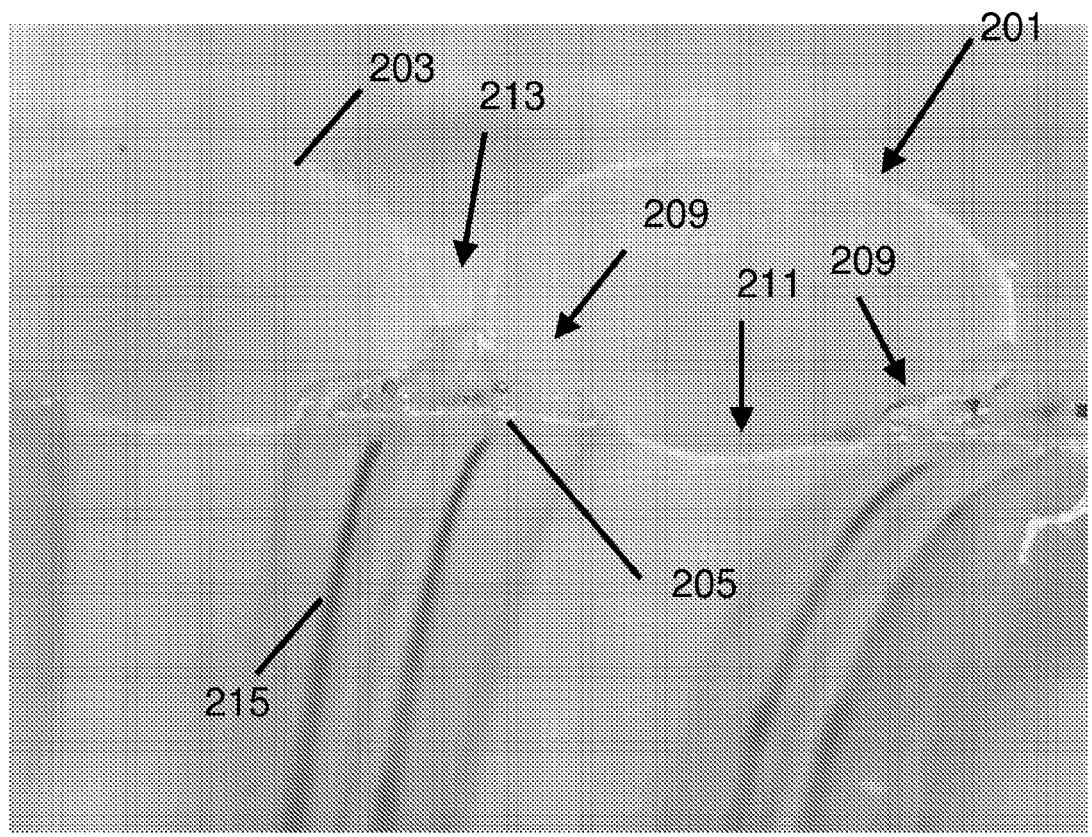
FIG. 2B shows a longitudinal cross-section of a top portion a tube similar to the example composite tube of FIG. 2A.

FIG. 2B shows a longitudinal cross-section of a top portion of the example composite tube 201 of FIG. 2A. FIG. 2B has the same orientation as FIG. 2A. This example further illustrates the hollow-body shape of the first elongate member 203. As seen in this example, the first elongate member 203 forms in longitudinal cross-section a plurality of hollow bubbles. Portions 209 of the first elongate member 203 overlap adjacent wraps of the second elongate member 205. A portion 211 of the first elongate member 203 forms the wall of the lumen (tube bore).

It was discovered that having a gap 213 between adjacent turns of the first elongate member 203, that is, between adjacent bubbles, unexpectedly improved the overall insulating properties of the composite tube 201. Thus, in certain embodiments, adjacent bubbles are separated by a gap 213. Furthermore, certain embodiments include the realization that providing a gap 213 between adjacent bubbles increases the heat transfer resistivity (the R value) and, accordingly, decreases the heat transfer conductivity of the composite tube 201. This gap configuration was also found to improve the flexibility of the composite tube 201 by permitting shorter-radius bends. A T-shaped second elongate member 205, as shown in FIG. 2B, can help maintain a gap 213 between adjacent bubbles. Nevertheless, in certain embodiments, adjacent bubbles are touching. For example, adjacent bubbles can be bonded together.

One or more conductive materials can be disposed in the second elongate member 205 for heating or sensing the gas flow. In this example, two heating filaments 215 are encapsulated in the second elongate member 205, one on either side of the vertical portion of the "T." The heating filaments 215 comprise conductive material, such as alloys of Aluminum (Al) and/or Copper (Cu), or conductive polymer. Preferably, the material forming the second elongate member 205 is selected to be non-reactive with the metal in the heating filaments 215 when the heating filaments 215 reach their operating temperature. The filaments 215 may be spaced away from lumen 207 so that the filaments are not exposed to the lumen 207. At one end of the composite tube, pairs of filaments can be formed into a connecting loop.

In at least one embodiment, a plurality of filaments are disposed in the second elongate member 205. The filaments can be electrically connected together to share a common rail. For example, a first filament, such as a heating filament, can be disposed on a first side of the second elongate member 205. A second filament, such as a sensing filament, can be disposed on a second side of the second elongate member 205. A third filament, such as a ground filament, can be disposed between the first and second filaments. The first, second, and/or third filaments can be connected together at one end of the second elongate member 205.

Figure 2C:
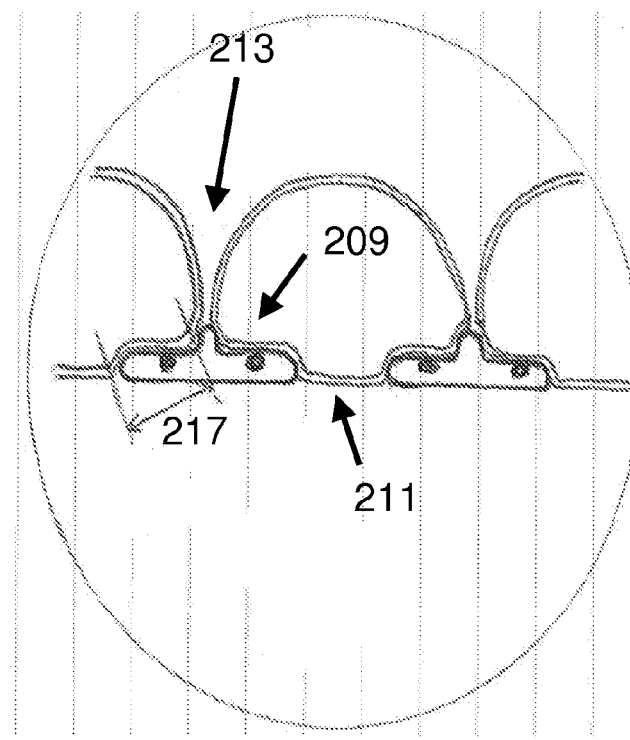
FIG. 2C shows another longitudinal cross-section illustrating a first elongate member in the composite tube.
Figure 2D:
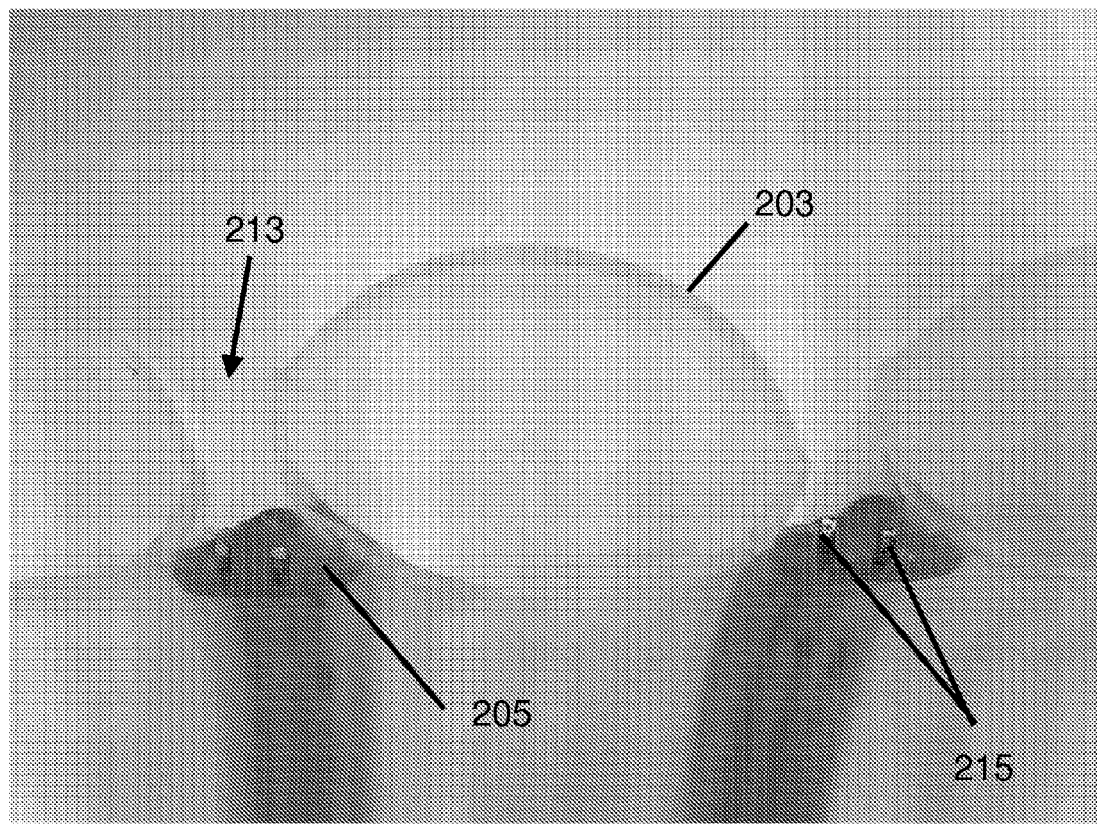
FIG. 2D shows another longitudinal cross-section of a top portion of a tube.
Figure 9A:
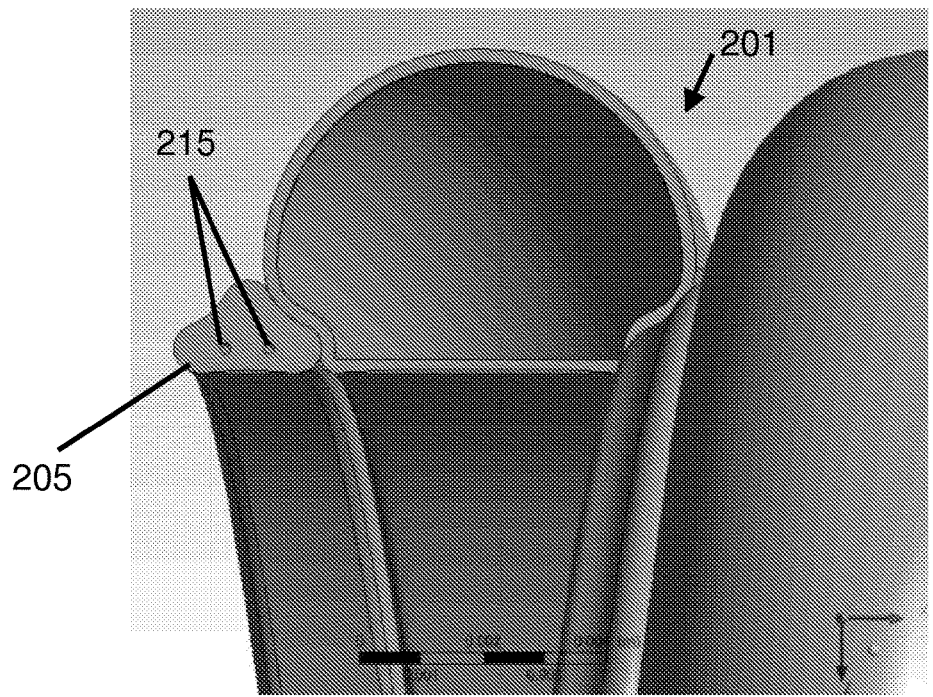
FIGS. 9A-C show examples of first elongate member shapes configured to improve thermal efficiency.
Figure 9B:
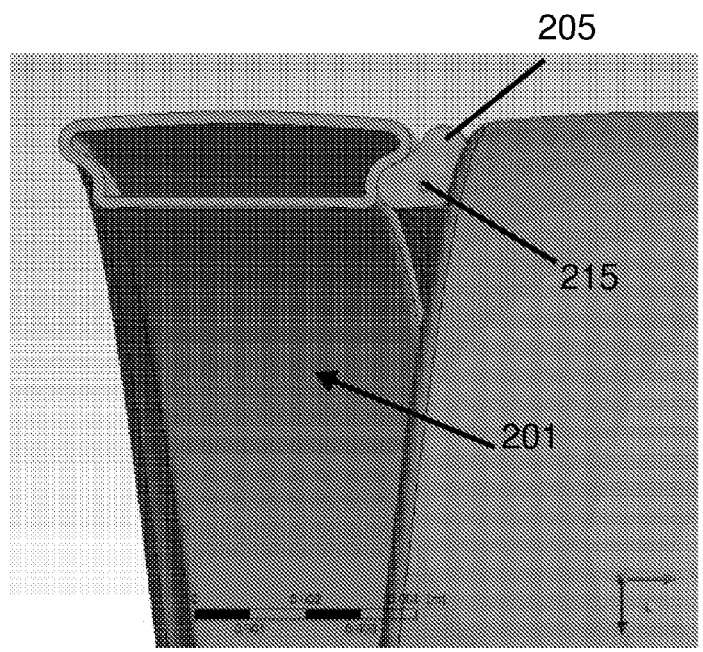
Figure 9C:
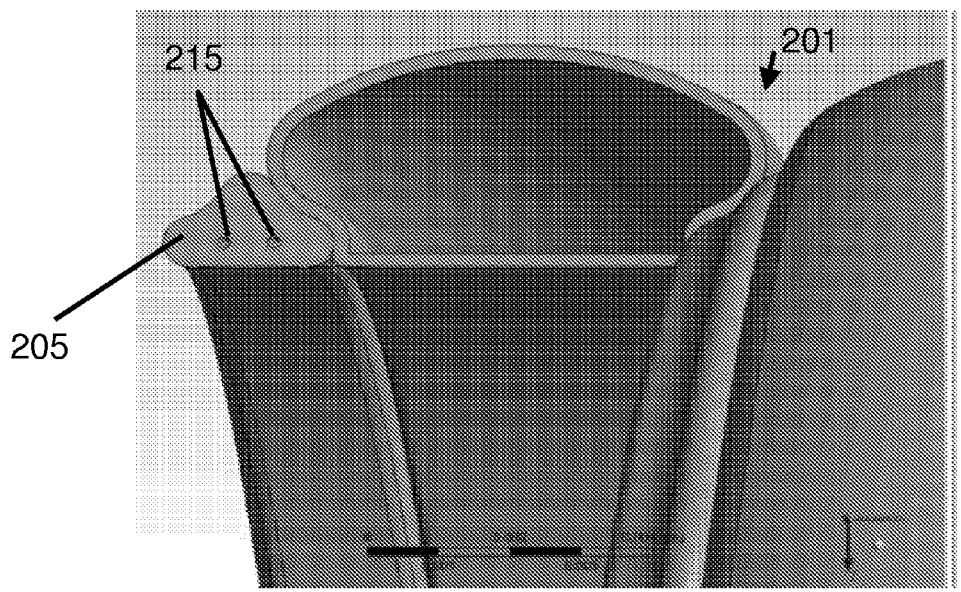

FIG. 2C shows a longitudinal cross-section of the bubbles in FIG. 2B. As shown, the portions 209 of the first elongate member 203 overlapping adjacent wraps of the second elongate member 205 are characterized by a degree of bond region 217. A larger bond region improves the tubes resistance to delamination at the interface of the first and second elongate members. Additionally or alternatively, the shape of the bead and/or the bubble can be adapted to increase the bond region 217. For example, FIG. 2D shows a relatively small bonding area on the left-hand side. FIG. 9B also demonstrates a smaller bonding region. In contrast, FIG. 2E has a much larger bonding region than that shown in FIG. 2D, because of the size and shape of the bead. FIGS. 9A and 9C also illustrate a larger bonding region. Each of these figures is discussed in more detail below. It should be appreciated that although the configurations in FIGS. 2E, 9A, and 9C may be preferred in certain embodiments, other configurations, including those of FIGS. 2D, 9B, and other variations, may be utilized in other embodiments as may be desired.

FIG. 2D shows a longitudinal cross-section of a top portion of another composite tube. FIG. 2D has the same orientation as FIG. 2B. This example further illustrates the hollow-body shape of the first elongate member 203 and demonstrates how the first elongate member 203 forms in longitudinal cross-section a plurality of hollow bubbles. In this example, the bubbles are completely separated from each other by a gap 213. A generally triangular second elongate member 205 supports the first elongate member 203.

Figure 2E:
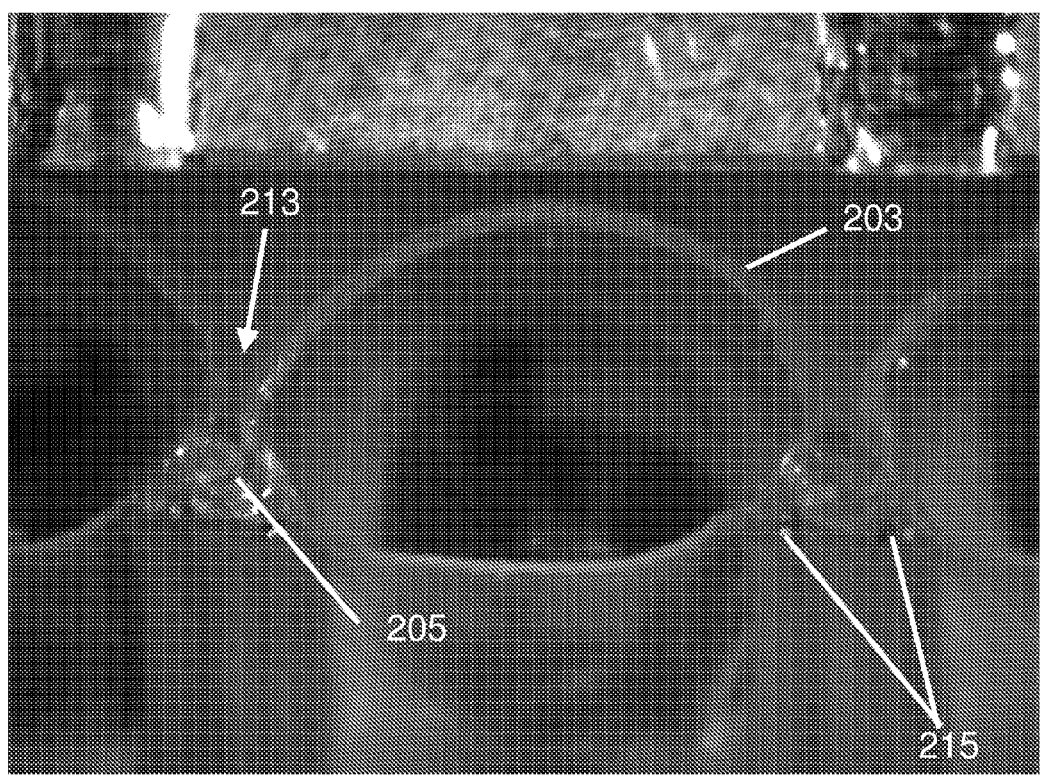
FIG. 2E shows another longitudinal cross-section of a top portion of a tube.

FIG. 2E shows a longitudinal cross-section of a top portion of another composite tube. FIG. 2E has the same orientation as FIG. 2B. In the example of FIG. 2E, the heating filaments 215 are spaced farther apart from each other than the filaments 215 in FIG. 2B. It was discovered that increasing the space between heating filaments can improve heating efficiency, and certain embodiments include this realization. Heating efficiency refers to the ratio of the amount of heat input to the tube to the amount of energy output or recoverable from the tube. Generally speaking, the greater the energy (or heat) that is dissipated from the tube, the lower the heating efficiency. For improved heating performance, the heating filaments 215 can be equally (or about equally) spaced along the bore of the tube. Alternatively, the filaments 215 can be positioned at extremities of the second elongate member 205, which may provide simpler manufacturing.

Figure 3A:
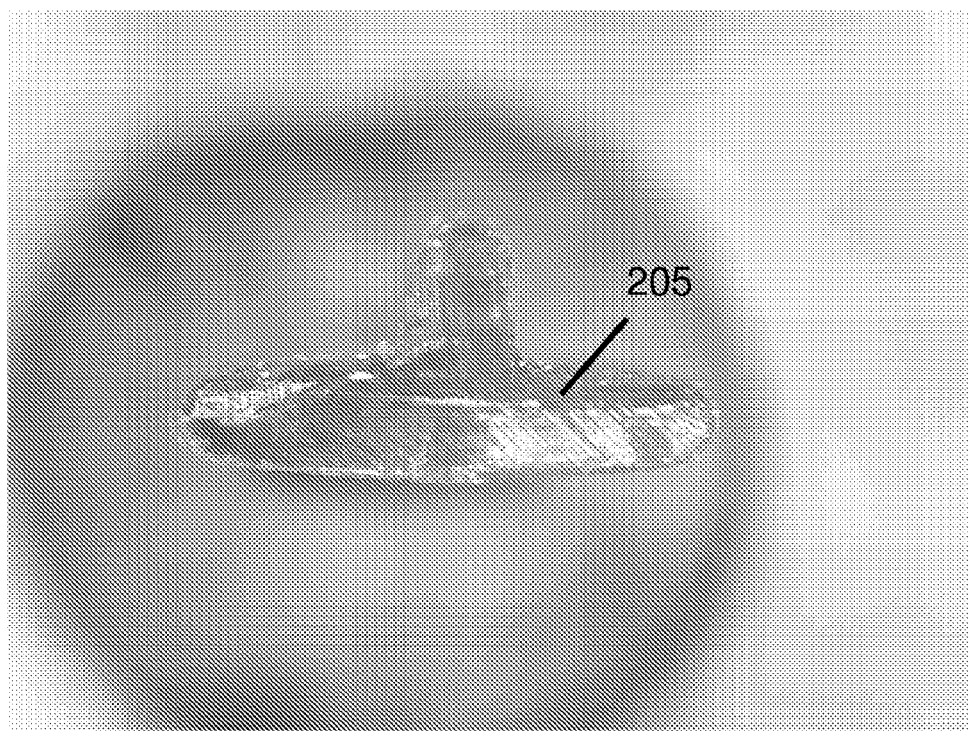
FIG. 3A shows a transverse cross-section of a second elongate member in the composite tube.

Reference is next made to FIGS. 3A through 3G which demonstrate example configurations for the second elongate member 205. FIG. 3A shows a cross-section of a second elongate member 205 having a shape similar to the T-shape shown in FIG. 2B. In this example embodiment, the second elongate member 205 does not have heating filaments. Other shapes for the second elongate member 205 may also be utilized, including variations of the T-shape as described below and triangular shapes.

Figure 3B:
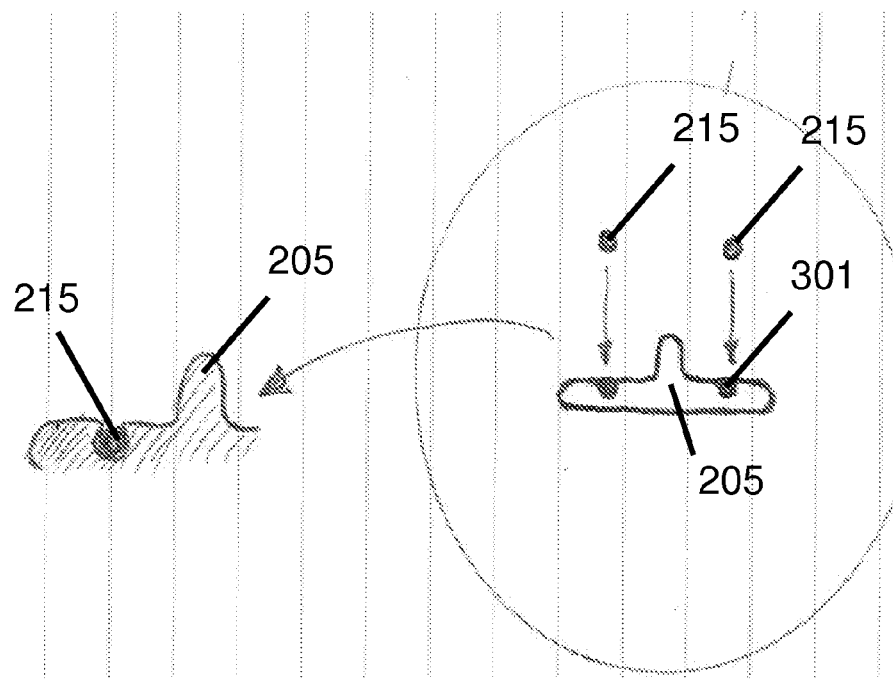
FIG. 3B shows another transverse cross-section of a second elongate member.

FIG. 3B shows another example second elongate member 205 having a T-shape cross-section. In this example, heating filaments 215 are embedded in cuts 301 in the second elongate member 205 on either side of the vertical portion of the "T." In some embodiments, the cuts 301 can be formed in the second elongate member 205 during extrusion. The cuts 301 can alternatively be formed in the second elongate member 205 after extrusion. For example, a cutting tool can form the cuts in the second elongate member 205. Preferably, the cuts are formed by the heating filaments 215 as they are pressed or pulled (mechanically fixed) into the second elongate member 205 shortly after extrusion, while the second elongate member 205 is relatively soft. Alternatively, one or more heating filaments can be mounted (e.g., adhered, bonded, or partially embedded) on the base of the elongate member, such that the filament(s) are exposed to the tube lumen. In such embodiments, it can be desirable to contain the filament(s) in insulation to reduce the risk of fire when a flammable gas such as oxygen is passed through the tube lumen.

Figure 3C:
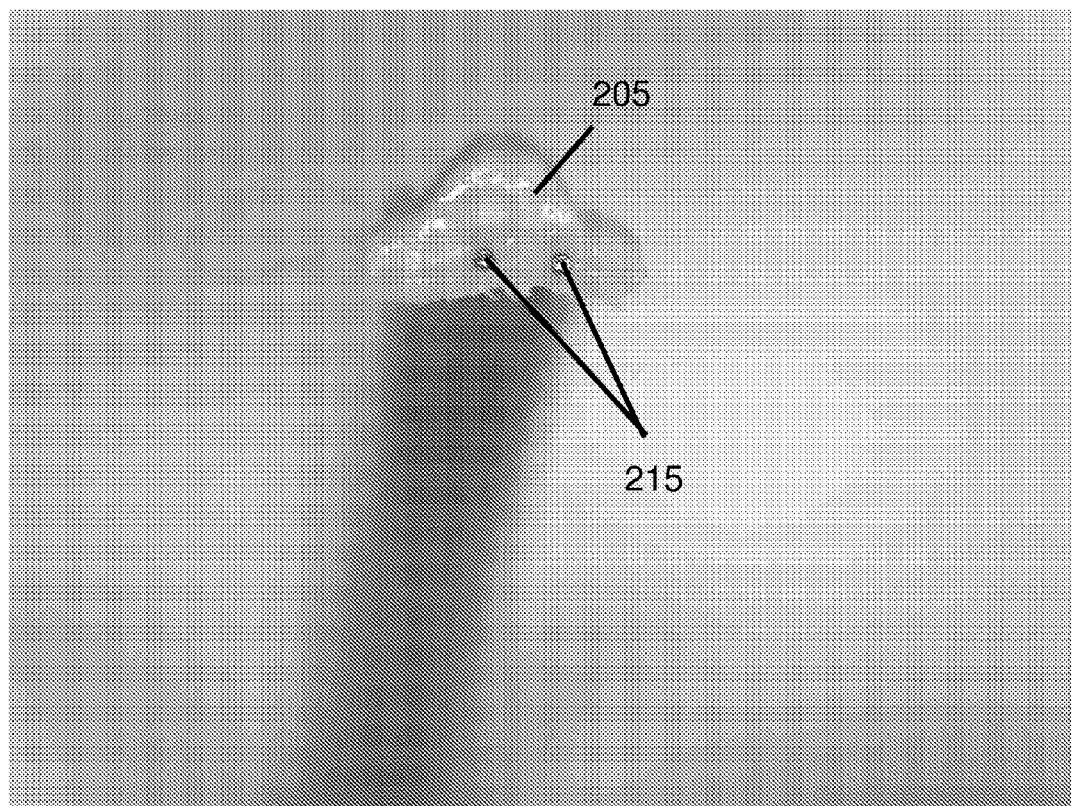
FIG. 3C shows another example second elongate member.

FIG. 3C shows yet another example second elongate member 205 in cross-section. The second elongate member 205 has a generally triangular shape. In this example, heating filaments 215 are embedded on opposite sides of the triangle.

Figure 3D:
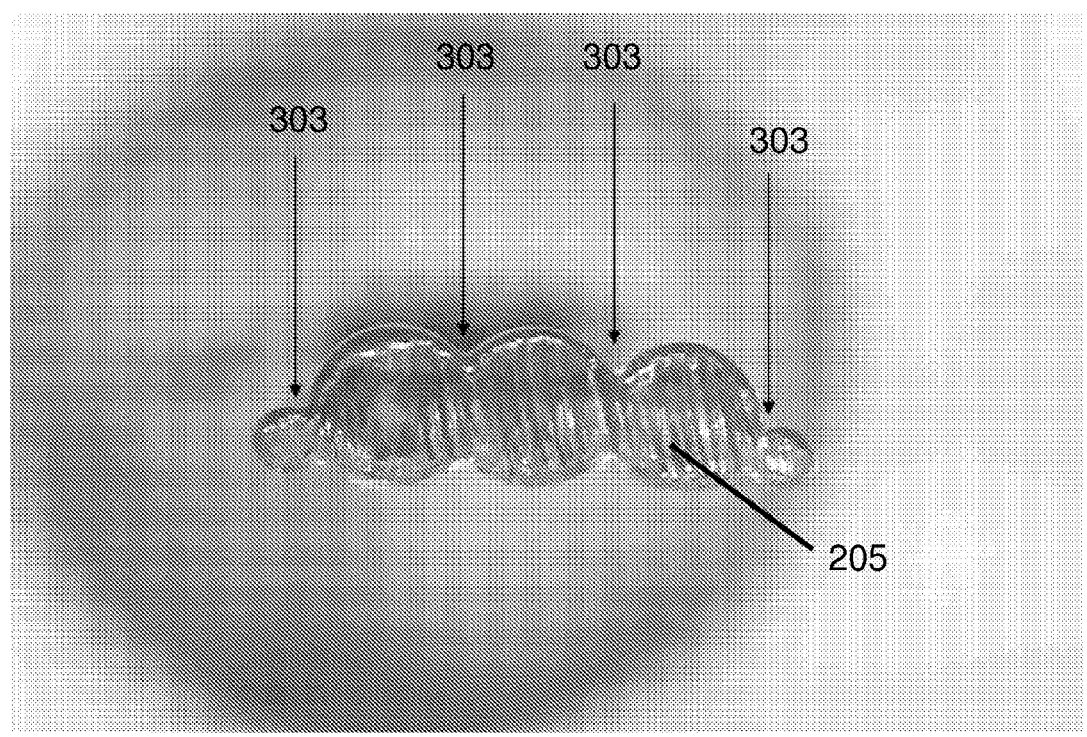
FIG. 3D shows another example second elongate member.

FIG. 3D shows yet another example second elongate member 205 in cross-section. The second elongate member 205 comprises four grooves 303. The grooves 303 are indentations or furrows in the cross-sectional profile. In some embodiments, the grooves 303 can facilitate the formation of cuts (not shown) for embedding filaments (not shown). In some embodiments, the grooves 303 facilitate the positioning of filaments (not shown), which are pressed or pulled into, and thereby embedded in, the second elongate member 205. In this example, the four initiation grooves 303 facilitate placement of up to four filaments, e.g., four heating filaments, four sensing filaments, two heating filaments and two sensing filaments, three heating filaments and one sensing filament, or one heating filament and three sensing filaments. In some embodiments, heating filaments can be located on the outside of the second elongate member 205. Sensing filaments can be located on the inside.

Figure 3E:
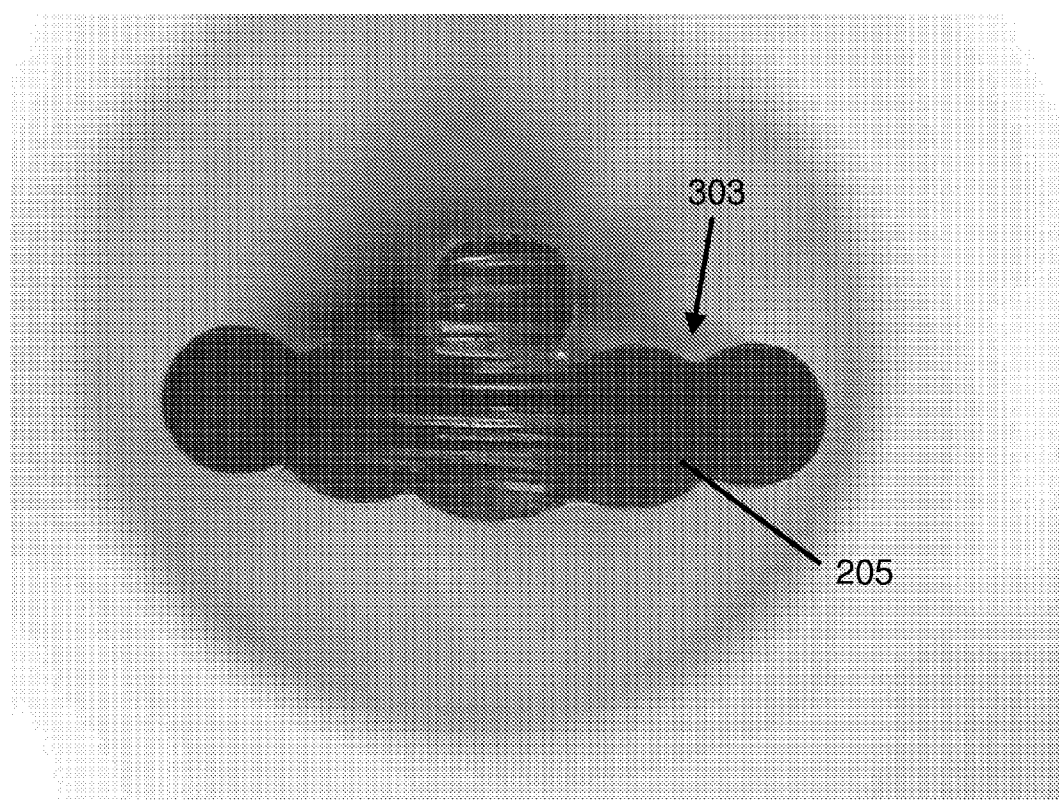
FIG. 3E shows another example second elongate member.

FIG. 3E shows still another example second elongate member 205 in cross-section. The second elongate member 205 has a T-shape profile and a plurality of grooves 303 for placing heating filaments.

Figure 3F:
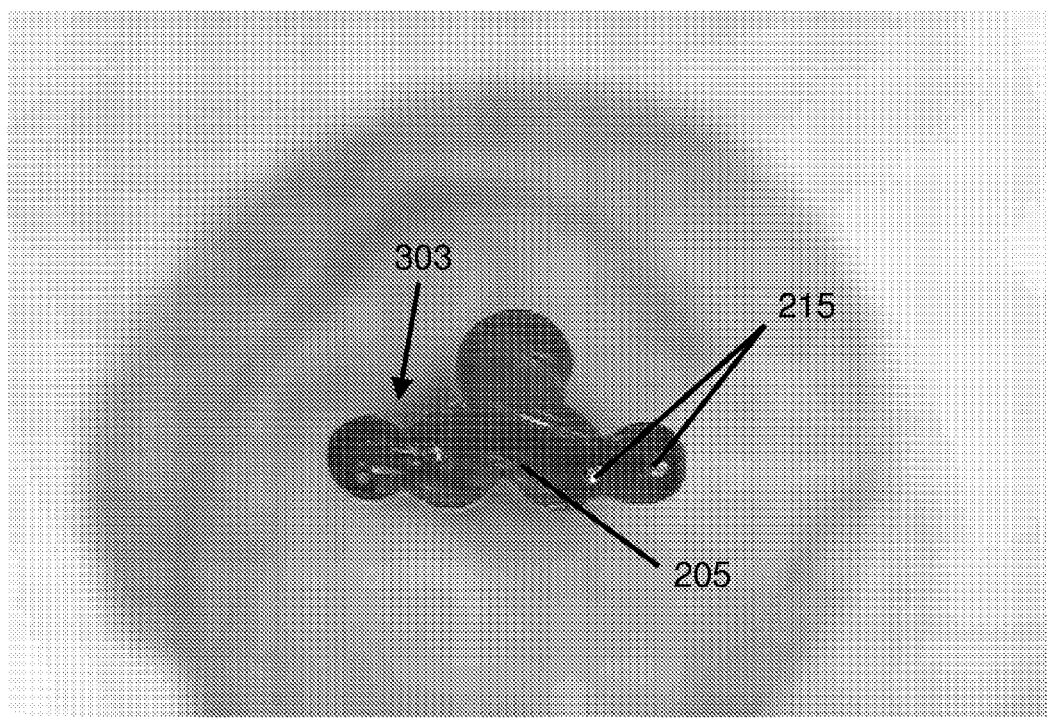
FIG. 3F shows another example second elongate member.

FIG. 3F shows yet another example second elongate member 205 in cross-section. Four filaments 215 are encapsulated in the second elongate member 205, two on either side of the vertical portion of the "T." As explained in more detail below, the filaments are encapsulated in the second elongate member 205 because the second elongate member 205 was extruded around the filaments. No cuts were formed to embed the heating filaments 215. In this example, the second elongate member 205 also comprises a plurality of grooves 303. Because the heating filaments 215 are encapsulated in the second elongate member 205, the grooves 303 are not used to facilitate formation of cuts for embedding heating filaments. In this example, the grooves 303 can facilitate separation of the embedded heating filaments, which makes stripping of individual cores easier when, for example, terminating the heating filaments.

Figure 3G:
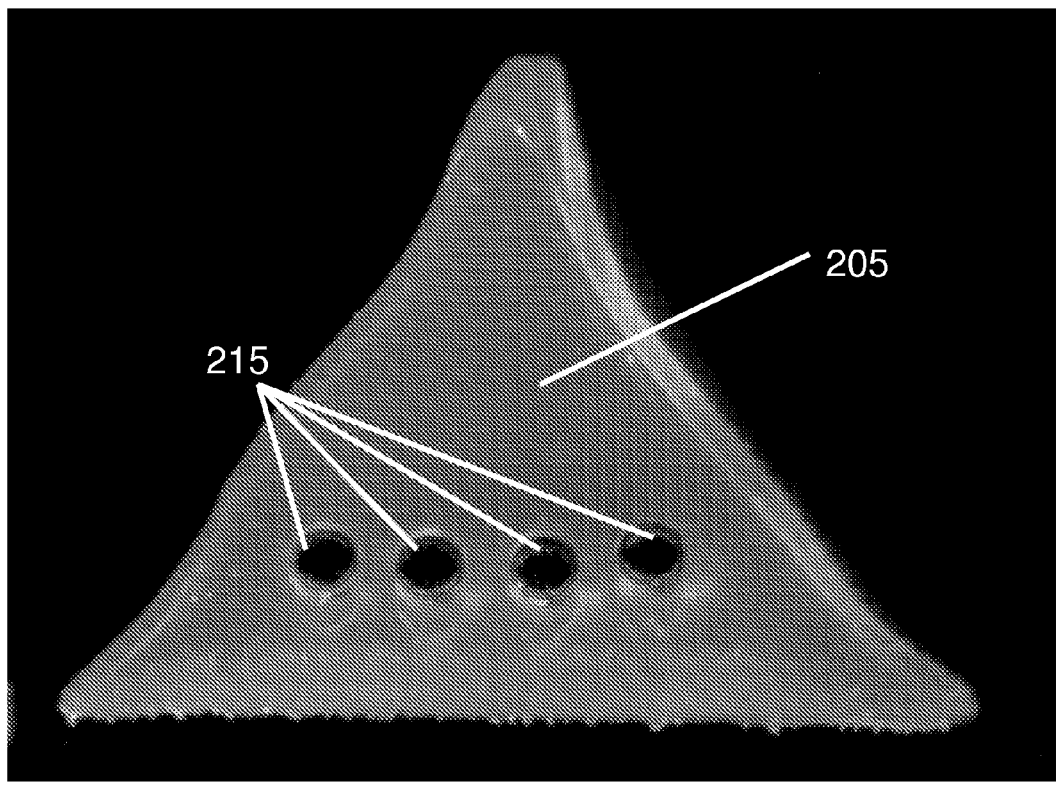
FIG. 3G shows another example second elongate member.

FIG. 3G shows yet another example second elongate member 205 in cross-section. The second elongate member 205 has a generally triangular shape. In this example, the shape of the second elongate member 205 is similar to that of FIG. 3C, but four filaments 215 are encapsulated in the second elongate member 205, all of which are central in the bottom third of the second elongate member 205 and disposed along a generally horizontal axis.

As explained above, it can be desirable to increase the distance between filaments to improve heating efficiency. In some embodiments, however, when heating filaments 215 are incorporated into the composite tube 201, the filaments 215 can be positioned relatively central in the second elongate member 205. A centralized position promotes robustness of the composite tubing for reuse, due in part to the position reducing the likelihood of the filament breaking upon repeating flexing of the composite tube 201. Centralizing the filaments 215 can also reduce the risk of an ignition hazard because the filaments 215 are coated in layers of insulation and removed from the gas path.

As explained above, some of the examples illustrate suitable placements of filaments 215 in the second elongate member 205. In the foregoing examples comprising more than one filament 215, the filaments 215 are generally aligned along a horizontal axis. Alternative configurations are also suitable. For example, two filaments can be aligned along a vertical axis or along a diagonal axis. Four filaments can be aligned along a vertical axis or a diagonal axis. Four filaments can be aligned in a cross-shaped configuration, with one filament disposed at the top of the second elongate member, one filament disposed at the bottom of the second elongate member (near the tube lumen), and two filaments disposed on opposite arms of a "T," "Y," or triangle base.

TABLES 1A and 1B show some preferred dimensions of medical tubes described herein, as well as some preferred ranges for these dimensions. The dimensions refer to a transverse cross-section of a tube. In these tables, lumen diameter represents the inner diameter of a tube. Pitch represents the distance between two repeating points measured axially along the tube, namely, the distance between the tip of the vertical portions of adjacent "T"s of the second elongate member. Bubble width represents the width (maximum outer diameter) of a bubble. Bubble height represents the height of a bubble from the tube lumen. Bead height represents the maximum height of the second elongate member from the tube lumen (e.g., the height of the vertical portion of the "T"). Bead width represents the maximum width of the second elongate member (e.g., the width of the horizontal portion of the "T"). Bubble thickness represents the thickness of the bubble wall.

TABLE 1A

| Feature | Infant Dimension (mm) | Infant Range (±) | Adult Dimension (mm) | Adult Range (±) |
|---|---|---|---|---|
| Lumen diameter | 11 | 1 | 18 | 5 |
| Pitch | 4.8 | 1 | 7.5 | 2 |
| Bubble width | 4.2 | 1 | 7 | 1 |
| Bead width | 2.15 | 1 | 2.4 | 1 |
| Bubble height | 2.8 | 1 | 3.5 | 0.5 |
| Bead height | 0.9 | 0.5 | 1.5 | 0.5 |
| Bubble thickness | 0.4 | 0.35 | 0.2 | 0.15 |

TABLE 1B

| Feature | Infant Dimension (mm) | Infant Range (±) | Adult Dimension (mm) | Adult Range (±) |
|---|---|---|---|---|
| Lumen diameter | 11 | 1 | 18 | 5 |
| Pitch | 4.8 | 1 | 7.5 | 2 |
| Bubble width | 4.2 | 1 | 7 | 1 |
| Bead width | 2.15 | 1 | 3.4 | 1 |
| Bubble height | 2.8 | 1 | 4.0 | 0.5 |
| Bead height | 0.9 | 0.5 | 1.7 | 0.5 |
| Bubble thickness | 0.4 | 0.35 | 0.2 | 0.15 |

TABLES 2A and 2B provide example ratios between the dimensions of tube features for the tubes described in TABLES 1A and 1B respectively.

TABLE 2A

| Ratios | Infant | Adult |
|---|---|---|
| Lumen diameter:Pitch | 2.3:1 | 2.4:1 |
| Pitch:Bubble width | 1.1:1 | 1.1:1 |
| Pitch:Bead width | 2.2:1 | 3.1:1 |
| Bubble width:Bead width | 2.0:1 | 2.9:1 |
| Lumen diameter:Bubble height | 3.9:1 | 5.1:1 |
| Lumen diameter:Bead height | 12.2:1 | 12.0:1 |
| Bubble height:Bead height | 3.1:1 | 2.3:1 |
| Lumen diameter:Bubble thickness | 27.5:1 | 90.0:1 |

TABLE 2B

| Ratios | Infant | Adult |
|---|---|---|
| Lumen diameter:Pitch | 2.3:1 | 2.4:1 |
| Pitch:Bubble width | 1.1:1 | 1.1:1 |
| Pitch:Bead width | 2.2:1 | 2.2:1 |
| Bubble width:Bead width | 2.0:1 | 2.1:1 |
| Lumen diameter:Bubble height | 3.9:1 | 4.5:1 |
| Lumen diameter:Bead height | 12.2:1 | 10.6:1 |

TABLE 2B-continued

| Ratios | Infant | Adult |
| --- | --- | --- |
| Bubble height:Bead height | 3.1:1 | 2.4 1 |
| Lumen diameter:Bubble thickness | 27.5:1 | 90.0:1 |

The following tables show some example properties of a composite tube (labeled "A"), described herein, having a heating filament integrated inside the second elongate member. For comparison, properties of a Fisher & Paykel model RT100 disposable corrugated tube (labeled "B") having a heating filament helically wound inside the bore of the tube are also presented.

Measurement of resistance to flow (RTF) was carried out according to Annex A of ISO 5367:2000(E). The results are summarized in TABLE 3. As seen below, the RTF for the composite tube is lower than the RTF for the model RT100 tube.

TABLE 3

| Flow rate | RTF (cm H$_2$O) | | | |
| --- | --- | --- | --- | --- |
| (L/min) | 3 | 20 | 40 | 60 |
| A | 0 | 0.05 | 0.18 | 0.38 |
| B | 0 | 0.28 | 0.93 | 1.99 |

Condensate or "rainout" within the tube refers to the weight of condensate collected per day at 20 L/min gas flow rate and room temperature of 18° C. Humidified air is flowed through the tube continuously from a chamber. The tube weights are recorded before and after each day of testing. Three consecutive tests are carried out with the tube being dried in between each test. The results are shown below in TABLE 4. The results showed that rainout is significantly lower in the composite tube than in the model RT100 tube.

TABLE 4

| Tube | A (Day 1) | A (Day 2) | A (Day 3) | B (Day 1) | B (Day 2) | B (day 3) |
| --- | --- | --- | --- | --- | --- | --- |
| Weight before (g) | 136.20 | 136.70 | 136.70 | 111.00 | 111.10 | 111.10 |
| Weight after (g) | 139.90 | 140.00 | 139.20 | 190.20 | 178.80 | 167.10 |
| Condensate weight (g) | 3.7 | 3.3 | 2.5 | 79.20 | 67.70 | 56.00 |

The power requirement refers to the power consumed during the condensate test. In this test, the ambient air was held at 18° C. Humidification chambers (see, e.g., the humidification chamber 129 in FIG. 1) were powered by MR850 heater bases. The heating filaments in the tubes were powered independently from a DC power supply. Different flow rates were set and the chamber was left to settle to 37° C. at the chamber output. Then, the DC voltage to the circuits was altered to produce a temperature of 40° C. at the circuit output. The voltage required to maintain the output temperature was recorded and the resulting power calculated. The results are shown in TABLE 5. The results show that composite Tube A uses significantly more power than Tube B. This is because Tube B uses a helical heating filament in the tube bore to heat the gas from 37° C. to 40° C. The composite tube does not tend to heat gas quickly because the heating filament is in the wall of the tube (embedded in the second elongate member). Instead, the composite tube is designed to maintain the gas temperature and prevent rainout by maintaining the tube bore at a temperature above the dew point of the humidified gas.

TABLE 5

| Flow rate (L/min) | 40 | 30 | 20 |
| --- | --- | --- | --- |
| Tube A, power required (W) | 46.8 | 38.5 | 37.8 |
| Tube B, power required (W) | 28.0 | 27.5 | 26.8 |

Tube flexibility was tested by using a three-point bend test. Tubes were placed in a three point bend test jig and used along with an Instron 5560 Test System instrument, to measure load and extension. Each tube sample was tested three times; measuring the extension of the tube against the applied load, to obtain average respective stiffness constants. The average stiffness constants for Tube A and Tube B are reproduced in TABLE 6.

TABLE 6

| Tube | Stiffness (N/mm) |
| --- | --- |
| A | 0.028 |
| B | 0.088 |

Methods of Manufacture

Reference is next made to FIGS. 4A through 4F which demonstrate example methods for manufacturing composite tubes.

Turning first to FIG. 4A, in at least one embodiment, a method of manufacturing a composite tube comprises providing the second elongate member 205 and spirally wrapping the second elongate member 205 around a mandrel 401 with opposite side edge portions 403 of the second elongate member 205 being spaced apart on adjacent wraps, thereby forming a second-elongate-member spiral 405. The second elongate member 205 may be directly wrapped around the mandrel in certain embodiments. In other embodiments, a sacrificial layer may be provided over the mandrel.

In at least one embodiment, the method further comprises forming the second elongate member 205. Extrusion is a suitable method for forming the second elongate member 205. The second extruder can be configured to extrude the second elongate member 205 with a specified bead height. Thus, in at least one embodiment, the method comprises extruding the second elongate member 205.

As shown in FIG. 4B, extrusion can be advantageous because it can allow heating filaments 215 to be encapsulated in the second elongate member 205 as the second elongate member is formed 205, for example, using an extruder having a cross-head extrusion die. Thus, in certain embodiments, the method comprises providing one or more heating filaments 215 and encapsulated the heating filaments 215 to form the second elongate member 205. The method can also comprise providing a second elongate member 205 having one or more heating filaments 215 embedded or encapsulated in the second elongate member 205.

In at least one embodiment, the method comprises embedding one or more filaments 215 in the second elongate member 205. For example, as shown in FIG. 4C, filaments 215 can be pressed (pulled or mechanically positioned) into the second elongate member 205 to a specified depth. Alternatively, cuts can be made in the second elongate member 205 to a specified depth, and the filaments 215 can be placed into the cuts. Preferably, pressing or cutting is done shortly after the second elongate member 205 is extruded and the second elongate member 205 is soft.

Figure 4D:
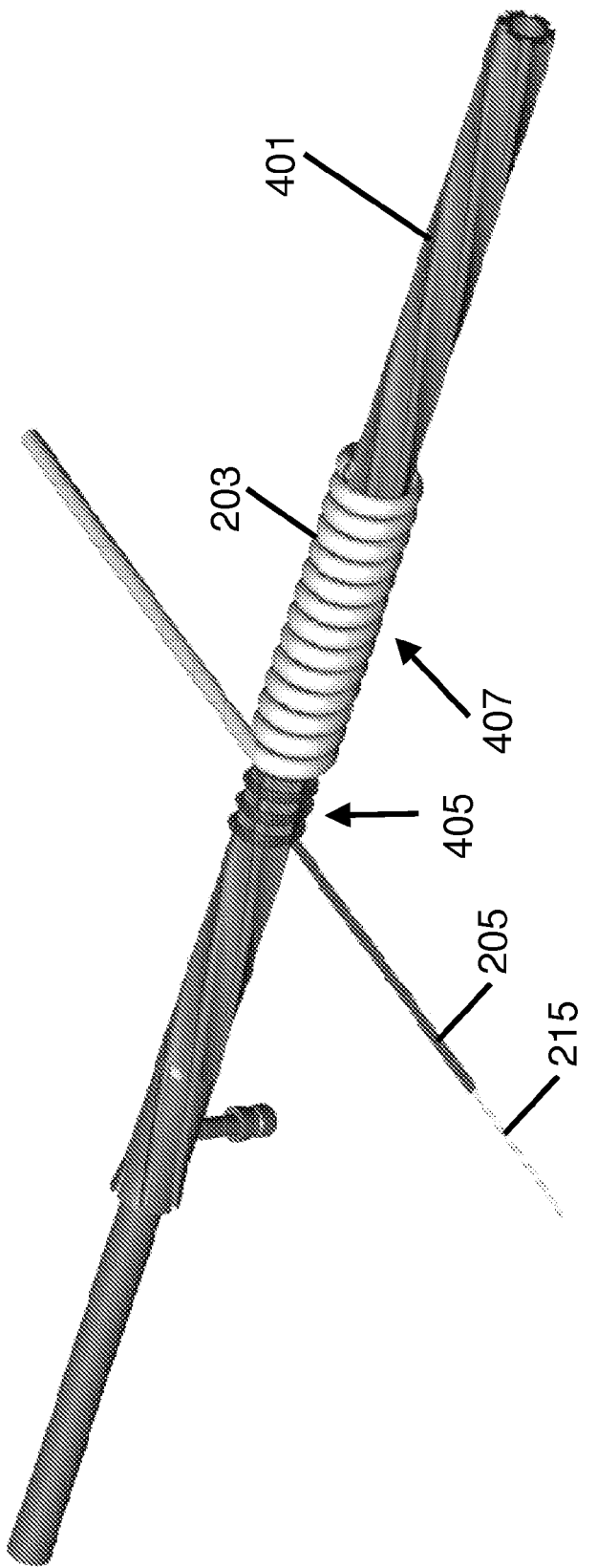
FIG. 4D shows another aspect in a method for forming the composite tube.
Figure 4E:
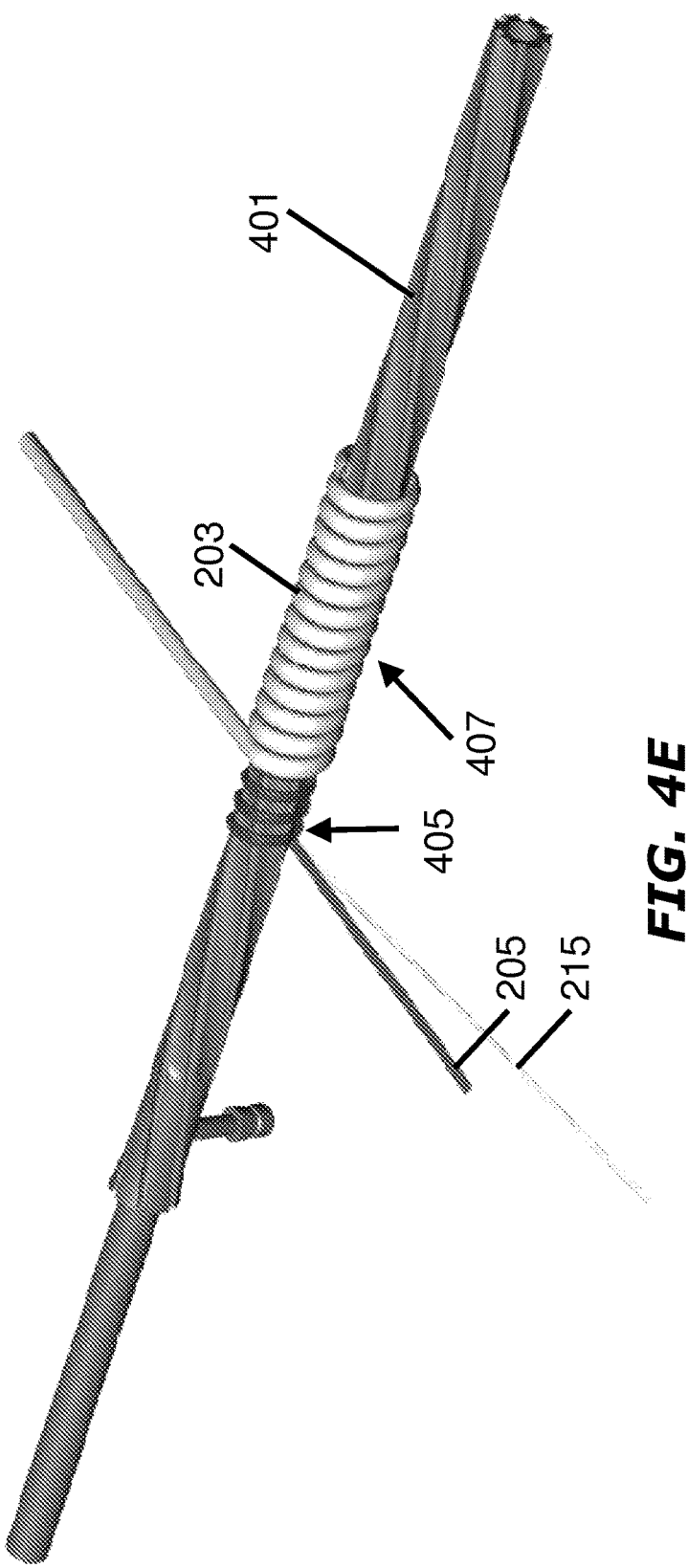
FIG. 4E shows another aspect in a method for forming the composite tube.

As shown in FIGS. 4D and 4E, in at least one embodiment, the method comprises providing the first elongate member 203 and spirally wrapping the first elongate member 203 around the second-elongate-member spiral 405, such that portions of the first elongate member 203 overlap adjacent wraps of the second-elongate-member spiral 405 and a portion of the first elongate member 203 is disposed adjacent the mandrel 401 in the space between the wraps of the second-elongate-member spiral 405, thereby forming a first-elongate-member spiral 407. FIG. 4D shows such an example method, in which heating filaments 215 are encapsulated in the second elongate member 205, prior to forming the second-elongate-member spiral. FIG. 4E shows such an example method, in which heating filaments 215 are embedded in the second elongate member 205, as the second-elongate-member spiral is formed. An alternative method of incorporating filaments 215 into the composite tube comprises encapsulating one or more filaments 215 between the first elongate member 203 and the second elongate member 205 at a region where the first elongate member 203 overlaps the second elongate member 205.

The above-described alternatives for incorporating one or more heating filaments 215 into a composite tube have advantages over the alternative of having heating filaments in the gas path. Having the heating filament(s) 215 out of the gas path improves performance because the filaments heat the tube wall where the condensation is most likely to form, This configuration reduces fire risk in high oxygen environments by moving the heating filament out of the gas path. This feature also reduces performance as it reduces the heating wires effectiveness at heating the gases that are passing through the tube. Nevertheless, in certain embodiments, a composite tube 201 comprises one or more heating filaments 215 placed within the gas path. For example, heating filaments can be emplaced on the lumen wall (tube bore), for example, in a spiral configuration. An example method for disposing one or more heating filaments 215 on the lumen wall comprises bonding, embedding, or otherwise forming a heating filament on a surface of the second elongate member 205 that, when assembled, forms the lumen wall. Thus, in certain embodiments, the method comprises disposing one or more heating filaments 215 on the lumen wall.

Regardless of whether the heating filaments 215 are embedded or encapsulated on the second elongate member 205 or disposed on the second elongate member 205, or otherwise placed in or on the tube, in at least one embodiment, pairs of filaments can be formed into a connecting loop at one end of the composite tube to form a circuit.

Figure 4F:
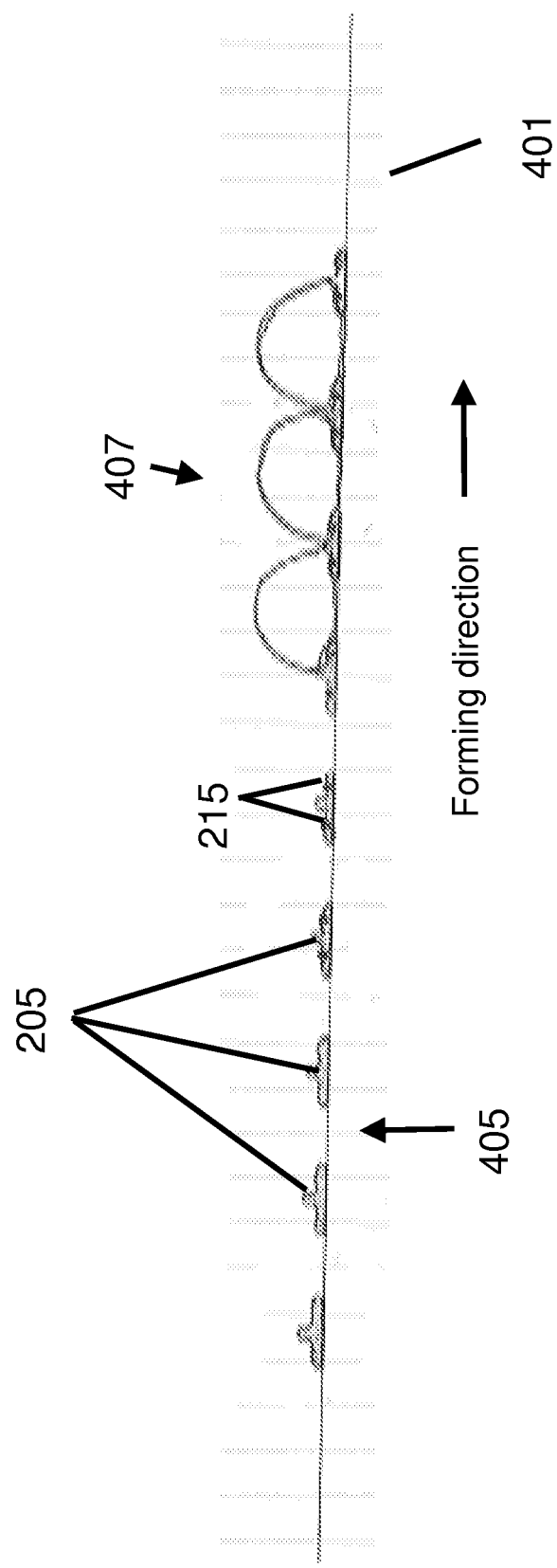
FIG. 4F shows another aspect in a method for forming the composite tube.

FIG. 4F shows a longitudinal cross-section of the assembly shown in FIG. 4E, focusing on a top portion of the mandrel 401 and a top portion of the first-elongate-member spiral 407 and second-elongate-member spiral 405. This example shows the second-elongate-member spiral 405 having a T-shaped second elongate member 205. As the second-elongate member is formed, heating filaments 215 are embedded in the second elongate member 205. The right side of FIG. 4F shows the bubble-shaped profile of the first-elongate-member spiral, as described above.

The method can also comprise forming the first elongate member 203. Extrusion is a suitable method for forming the first elongate member 203. Thus, in at least one embodiment, the method comprises extruding the first elongate member 203. The first elongate member 203 can also be manufactured by extruding two or more portions and joining them to form a single piece. As another alternative, the first elongate member 203 can also be manufactured by extruding sections that produce a hollow shape when formed or bonded adjacently on a spiral-tube forming process.

The method can also comprise supplying a gas at a pressure greater than atmospheric pressure to an end of the first elongate member 203. The gas can be air, for example. Other gases can also be used, as explained above. Supplying a gas to an end of the first elongate member 203 can help maintain an open, hollow body shape as the first elongate member 203 is wrapped around the mandrel 401. The gas can be supplied before the first elongate member 203 is wrapped around the mandrel 401, while the first elongate member 203 is wrapped around the mandrel 401, or after the first elongate member 203 is wrapped around the mandrel 401. For instance, an extruder with an extrusion die head/tip combination can supply or feed air into the hollow cavity of the first elongate member 203 as the first elongate member 203 is extruded. Thus, in at least one embodiment, the method comprises extruding the first elongate member 203 and supplying a gas at a pressure greater than atmospheric pressure to an end of the first elongate member 203 after extrusion. A pressure of 15 to 30 cm $H_2O$—(or about 15 to 30 cm $H_2O$) has been found to be suitable.

In at least one embodiment, the first elongate member 203 and the second elongate member 205 are spirally wound about the mandrel 401. For example, the first elongate member 203 and second elongate member 205 may come out of an extrusion die at an elevated temperature of 200° C. (or about 200° C.) or more and then be applied to the mandrel after a short distance. Preferably, the mandrel is cooled using a water jacket, chiller, and/or other suitable cooling method to a temperature of 20° C. (or about 20° C.) or less, e.g., approaching 0° C. (or about 0° C.). After 5 (or about 5) spiral wraps, the first elongate member 203 and second elongate member 205 are further cooled by a cooling fluid (liquid or gas). In one embodiment, the cooling fluid is air emitted from a ring with jets encircling the mandrel. After cooling and removing the components from the mandrel, a composite tube is formed having a lumen extending along a longitudinal axis and a hollow space surrounding the lumen. In such an embodiment, no adhesive or other attachment mechanism is needed to connect the first and second elongate members. Other embodiments may utilize an adhesive or other attachment mechanism to bond or otherwise connect the two members. In another embodiment, the second elongate member 205 after extrusion and placement of the heating filaments may be cooled to freeze the location of the heating filaments. The second elongate member 205 may then be re-heated when applied to the mandrel to improve bonding. Example methods for re-heating include using spot-heating devices, heated rollers, etc.

The method can also comprise formed pairs of heating or sensing filaments into a connecting loop at one end of the composite tube. For example, end sections of two heating or sensing filaments can be extricated from the second elongate member 205 and then formed into a connecting loop e.g., by tying, bonding, adhering, fusing, etc the two filaments together. As another example, end sections of the heating filaments can be left free from the second elongate member 205 during the manufacturing process and then formed into a connecting loop when the composite tube is assembled.

Medical Tubes and Methods of Manufacture Using a Single Spirally Wound Tube

Reference is next made to FIG. 5A through 5F which show transverse cross-sections of tubes comprising a single tube-shaped element having a first elongate member or portion 203 and a second elongate member or portion 205A. As illustrated, the second elongate portions 205A are integral with the first elongate portions 203, and extend along the entire length of the single tube-shaped element. In the embodiments illustrated, the single tube-shaped element is an elongate hollow body having in transverse cross-section a relatively thin wall defining in part the hollow portion 501, with two reinforcement portions 205A with a relatively greater thickness or relatively greater rigidity on opposite sides of the elongate hollow body adjacent the relatively thin wall. These reinforcement portions form a portion of the inner wall of the lumen 207 after the elongate hollow body is spirally wound, such that these reinforcement portions are also spirally positioned between adjacent turns of the elongate hollow body.

In at least one embodiment, the method comprises forming an elongate hollow body comprising the first elongate portion 203 and the reinforcement portion 205A. Extrusion is a suitable method for forming the elongate hollow body. Suitable cross-sectional shapes for the tube-shaped element are shown in FIG. 5A through 5F.

The elongate hollow body can be formed into a medical tube, as explained above, and the foregoing discussion is incorporated by this reference. For example, in at least one embodiment, a method of manufacturing a medical tube comprises spirally wrapping or winding the elongate hollow body around a mandrel. This may be done at an elevated temperature, such that the elongate hollow body is cooled after being spirally wound to join adjacent turns together As shown in FIG. 5B, opposite side edge portions of the reinforcement portions 205A can touch on adjacent turns. In other embodiments, opposite side edge portions of the second elongate member 205A can overlap on adjacent turns, as shown in FIGS. 5D and 5E. Heating filaments 215 can be incorporated into the second elongate member as explained above and as shown in FIG. 5A through 5F. For example, heating filaments may be provided on opposite sides of the elongate hollow body such as shown in FIGS. 5A-5D. Alternatively, heating filaments may be provided on only one side of the elongate hollow body, such as shown in FIGS. 5E-5F. Any of these embodiments could also incorporate the presence of sensing filaments.

Medical Circuits

Figure 6:
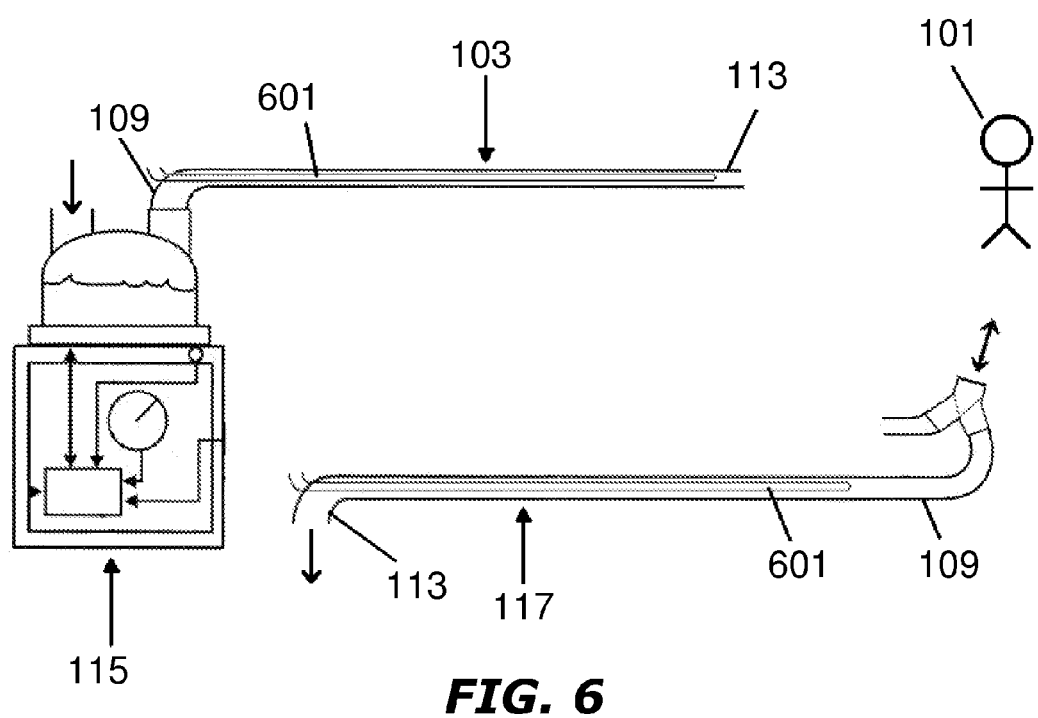
FIG. 6 shows an example medical circuit according to at least one embodiment.

Reference is next made to FIG. 6, which shows an example medical circuit according to at least one embodiment. The circuit comprises one or more composite tubes as described above, namely for the inspiratory tube 103 and/or the expiratory tube 117. The properties of the inspiratory tube 103 and the expiratory tube 117 are similar to the tubes described above with respect to FIG. 1. The inspiratory tube 103 has an inlet 109, communicating with a humidifier 115, and an outlet 113, through which humidified gases are provided to the patient 101. The expiratory tube 117 also has an inlet 109, which receives exhaled humidified gases from the patient, and an outlet 113. As described above with respect to FIG. 1, the outlet 113 of the expiratory tube 117 can vent exhaled gases to the atmosphere, to the ventilator/blower unit 115, to an air scrubber/filter (not shown), or to any other suitable location.

As described above, heating filaments 601 can be placed within the inspiratory tube 103 and/or the expiratory tube 117 to reduce the risk of rain out in the tubes by maintaining the tube wall temperature above the dew point temperature.

Component of an Insufflation System

Laparoscopic surgery, also called minimally invasive surgery (MIS), or keyhole surgery, is a modern surgical technique in which operations in the abdomen are performed through small incisions (usually 0.5 to 1.5 cm) as compared to larger incisions needed in traditional surgical procedures. Laparoscopic surgery includes operations within the abdominal or pelvic cavities. During laparoscopic surgery with insufflation, it may be desirable for the insufflation gas (commonly $CO_2$) to be humidified before being passed into the abdominal cavity. This can help prevent "drying out" of the patient's internal organs, and can decrease the amount of time needed for recovery from surgery. Insufflation systems generally comprise humidifier chambers that hold a quantity of water within them. The humidifier generally includes a heater plate that heats the water to create a water vapour that is transmitted into the incoming gases to humidify the gases. The gases are transported out of the humidifier with the water vapor.

Figure 7:
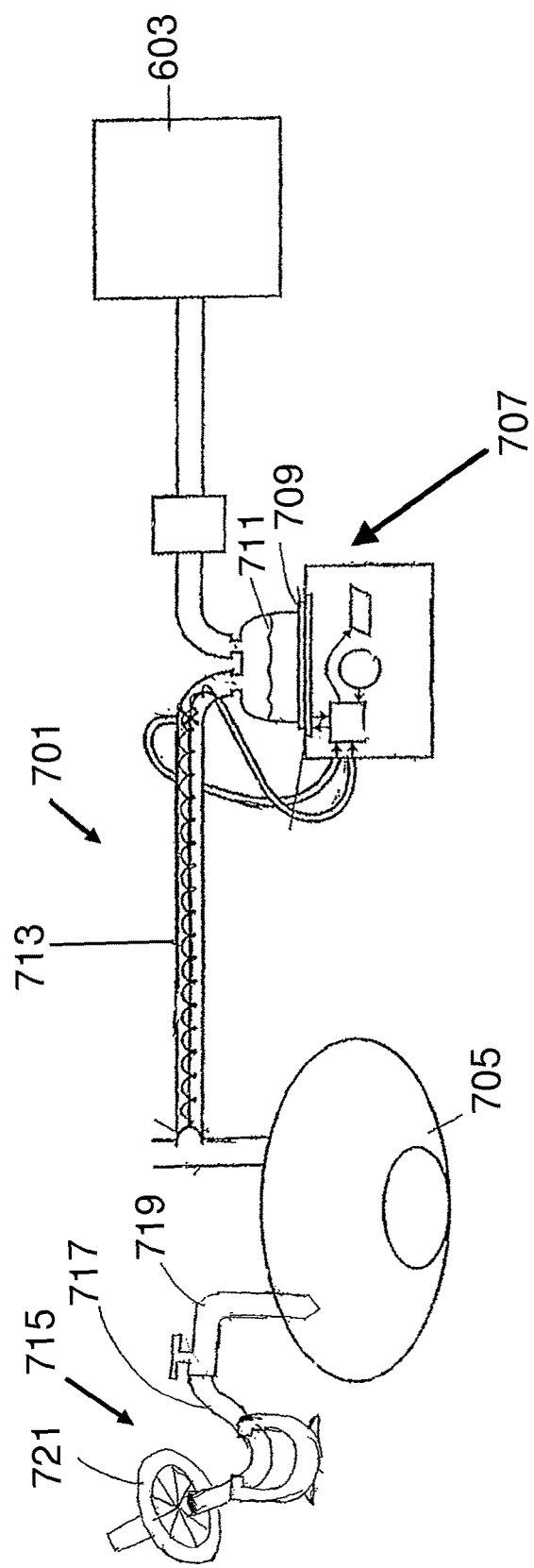
FIG. 7 shows an insufflation system according to at least one embodiment.
Figure 8:
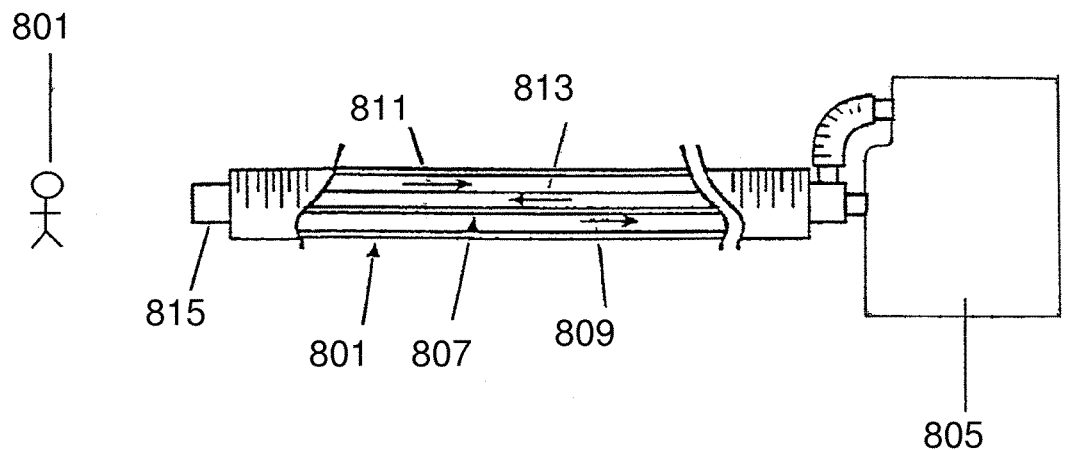
FIG. 8 is a schematic illustration of a coaxial tube, according to at least one embodiment.

Reference is next made to FIG. 7, which shows an insufflation system 701, according to at least one embodiment. The insufflation system 701 includes an insufflator 703 that produces a stream of insufflation gases at a pressure above atmospheric for delivery into the patient 705 abdominal or peritoneal cavity. The gases pass into a humidifier 707, including a heater base 709 and humidifier chamber 711, with the chamber 711 in use in contact with the heater base 709 so that the heater base 709 provides heat to the chamber 711. In the humidifier 707, the insufflation gases are passed through the chamber 711 so that they become humidified to an appropriate level of moisture.

The system 701 includes a delivery conduit 713 that connects between the humidifier chamber 711 and the patient 705 peritoneal cavity or surgical site. The conduit 713 has a first end and second end, the first end being connected to the outlet of the humidifier chamber 711 and receiving humidified gases from the chamber 711. The second end of the conduit 713 is placed in the patient 705 surgical site or peritoneal cavity and humidified insufflation gases travel from the chamber 711, through the conduit 713 and into the surgical site to insufflate and expand the surgical site or peritoneal cavity. The system also includes a controller (not shown) that regulates the amount of humidity supplied to the gases by controlling the power supplied to the heater base 709. The controller can also be used to monitor water in the humidifier chamber 711. A smoke evacuation system 715 is shown leading out of the body cavity of the patient 705.

The smoke evacuation system 715 can be used in conjunction with the insufflation system 701 described above or may be used with other suitable insufflation systems. The smoke evacuation system 715 comprises a discharge or exhaust limb 717, a discharge assembly 719, and a filter 721. The discharge limb 717 connects between the filter 721 and the discharge assembly 719, which in use is located in or adjacent to the patient 705 surgical site or peritoneal cavity. The discharge limb 717 is a self-supporting tube (that is, the tube is capable of supporting its own weight without collapsing) with two open ends: an operative site end and an outlet end.

At least one embodiment includes the realization that the use of a composite tube as the conduit 713 can deliver humidified gases to the patient 705 surgical site with minimized heat loss. This can advantageously reduce overall energy consumption in the insufflation system, because less heat input is needed to compensate for heat loss.

Coaxial Tube

A coaxial breathing tube can also comprise a composite tube as described above. In a coaxial breathing tube, a first gas space is an inspiratory limb or an expiratory limb, and the second gas space is the other of the inspiratory limb or expiratory limb. One gas passageway is provided between the inlet of said inspiratory limb and the outlet of said inspiratory limb, and one gas passageway is provided between the inlet of said expiratory limb and the outlet of said expiratory limb. In one embodiment, the first gas space is said inspiratory limb, and the second gas space is said expiratory limb. Alternatively, the first gas space can be the expiratory limb, and the second gas space can be the inspiratory limb.

Reference is next made to FIG. 7, which shows a coaxial tube 701 according to at least one embodiment. In this example, the coaxial tube 701 is provided between a patient 701 and a ventilator 705. Expiratory gases and inspiratory gases each flow in one of the inner tube 707 or the space 709 between the inner tube 707 and the outer tube 711. It will be appreciated that the outer tube 711 may not be exactly aligned with the inner tube 707. Rather, "coaxial" refers to a tube situated inside another tube.

For heat transfer reasons, the inner tube 707 can carry the inspiratory gases in the space 713 therewithin, while the expiratory gases are carried in the space 709 between the inner tube 707 and the outer tube 711. This airflow configuration is indicated by arrows. However, a reverse configuration is also possible, in which the outer tube 711 carries inspiratory gases and the inner tube 707 carries expiratory gases.

In at least one embodiment, the inner tube 707 is formed from a corrugated tube, such as a Fisher & Paykel model RT100 disposable tube. The outer tube 711 can be formed from a composite tube, as described above.

With a coaxial tube 701, the ventilator 705 may not become aware of a leak in the inner tube 707. Such a leak may short circuit the patient 701, meaning that the patient 701 will not be supplied with sufficient oxygen. Such a short circuit may be detected by placement of a sensor at the patient end of the coaxial tube 701. This sensor may be located in the patient end connector 715. A short circuit closer to the ventilator 705 will lead to continued patient 701 re-breathing of the air volume close to the patient 701. This will lead to a rise in the concentration of carbon dioxide in the inspiratory flow space 713 close to the patient 701, which can be detected directly by a $CO_2$ sensor. Such a sensor may comprise any one of a number of such sensors as is currently commercially available. Alternatively, this re-breathing may be detected by monitoring the temperature of the gases at the patient end connector 715, wherein a rise in temperature above a predetermined level indicates that re-breathing is occurring.

In addition to the above to reduce or eliminate the formation of condensation within either the inner tube 707 or outer tube 711, and to maintain a substantially uniform temperature in the gases flow through the coaxial tube 701, a heater, such as a resistance heater filament, may be provided within either the inner tube 707 or outer tube 711, disposed within the gases spaces 709 or 713, or within the inner tube 707 or outer tube 711 walls themselves.

Thermal Properties

In embodiments of a composite tube 201 incorporating a heating filament 215, heat can be lost through the walls of the first elongate member 203, resulting in uneven heating. As explained above, one way to compensate for these heat losses is to apply an external heating source at the first elongate member 203 walls, which helps to regulate the temperature and counter the heat loss. Other methods for optimizing thermal properties can also be used, however.

Reference is next made to FIGS. 9A through 9C, which demonstrate example configurations for bubble height (that is, the cross-sectional height of the first elongate member 203 measured from the surface facing the inner lumen to the surface forming the maximum outer diameter) to improve thermal properties.

The dimensions of the bubble can be selected to reduce heat loss from the composite tube 201. Generally, increasing the height of the bubble increases the effective thermal resistance of the tube 201, because a larger bubble height permits the first elongate member 203 to hold more insulating air. However, it was discovered that, at a certain bubble height, changes in air density cause convection inside the tube 201, thereby increasing heat loss. Also, at a certain bubble height the surface area becomes so large that the heat lost through surface outweighs the benefits of the increased height of the bubble. Certain embodiments include these realizations.

The radius of curvature and the curvature of the bubble can be useful for determining a desirable bubble height. The curvature of an object is defined as the inverse of the radius of curvature of that object. Therefore, the larger a radius of curvature an object has, the less curved the object is. For example, a flat surface would have a radius of curvature of ∞, and therefore a curvature of 0.

FIG. 9A shows a longitudinal cross-section of a top portion of a composite tube. FIG. 9A shows an embodiment of a composite tube 201 where the bubble has a large height. In this example, the bubble has a relatively small radius of curvature and therefore a large curvature. Also, the bubble is approximately three to four times greater in height than the height of the second elongate member 205.

FIG. 9B shows a longitudinal cross-section of a top portion of another composite tube. FIG. 9B shows an embodiment of a composite tube 201 where the bubble is flattened on top. In this example, the bubble has a very large radius of curvature but a small curvature. Also, the bubble is approximately the same height as the second elongate member 205.

FIG. 9C shows a longitudinal cross-section of a top portion of another composite tube. FIG. 9C shows an embodiment of a composite tube 201 where the width of the bubble is greater than the height of the bubble. In this example, the bubble has radius of curvature and the curvature between that of FIG. 9A and FIG. 9B, and the center of the radius for the upper portion of the bubble is outside of the bubble (as compared to FIG. 9A). The inflection points on the left and right sides of the bubble are about at the middle (heightwise) of the bubble (as opposed to in the lower portion of the bubble, as in FIG. 9A). Also, the height of the bubble is approximately double that of the second elongate member 205, resulting in a bubble height between that of FIG. 9A and FIG. 9B.

The configuration of FIG. 9A resulted in the lowest heat loss from the tube. The configuration of FIG. 9B resulted in the highest heat loss from the tube. The configuration of FIG. 9C had intermediate heat loss between the configurations of FIGS. 9A and 9B. However, the large external surface area and convective heat transfer in the configuration of FIG. 9A led to inefficient heating. Thus, of the three bubble arrangements of FIGS. 9A-9C, FIG. 9C was determined to have the best overall thermal properties. When the same thermal energy was input to the three tubes, the configuration of FIG. 9C allowed for the largest temperature rise along the length of the tube. The bubble of FIG. 9C is sufficiently large to increase the insulating air volume, but not large enough to cause a significant convective heat loss. The configuration of FIG. 9B was determined to have the poorest thermal properties, namely that the configuration of FIG. 9B allowed for the smallest temperature rise along the length of the tube. The configuration of FIG. 9A had intermediate thermal properties and allowed for a lower temperature rise than the configuration of FIG. 9C.

It should be appreciated that although the FIG. 9C configuration may be preferred in certain embodiments, other configurations, including those of FIGS. 9A, 9B and other variations, may be utilized in other embodiments as may be desired.

TABLE 7 shows the height of the bubble, the outer diameter of the tube, and the radius of curvature of the configurations shown in each of FIGS. 9A, 9B, and 9C.

TABLE 7

|  | Tube (FIG.) | | |
| --- | --- | --- | --- |
|  | 9A | 9B | 9C |
| Bubble height (mm) | 3.5 | 5.25 | 1.75 |
| Outer diameter (mm) | 21.5 | 23.25 | 19.75 |
| Radius of curvature (mm) | 5.4 | 3.3 | 24.3 |

Figure 11A:
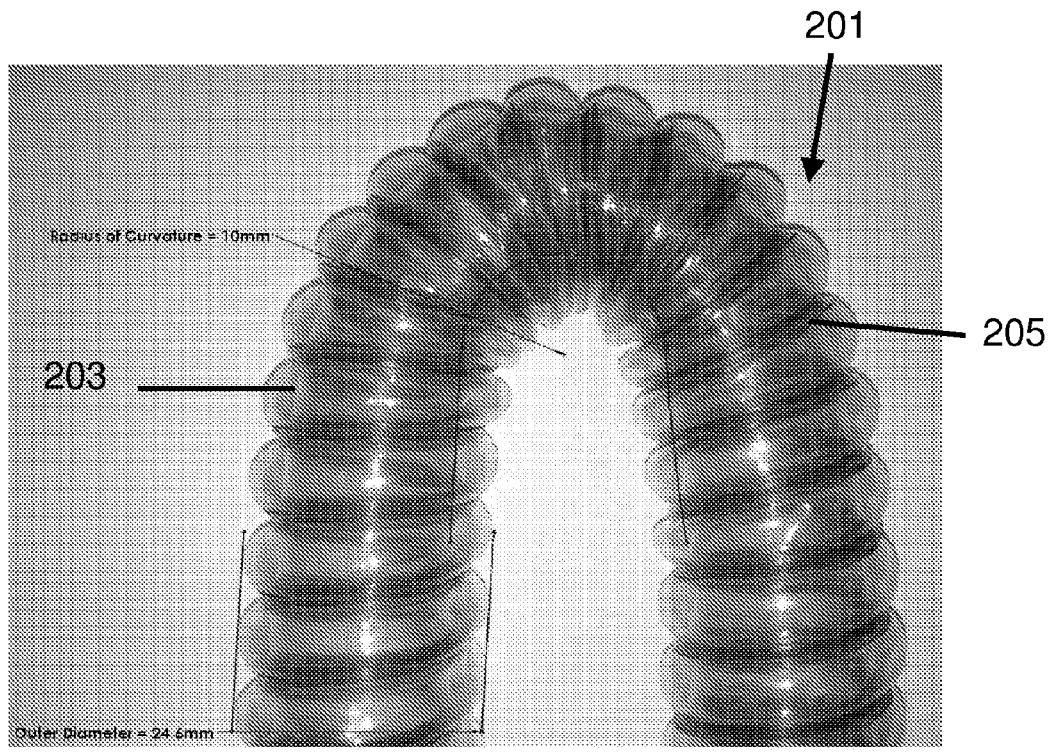
FIGS. 11A-D demonstrate radius of curvature properties of tubes according to various embodiments.
Figure 11B:
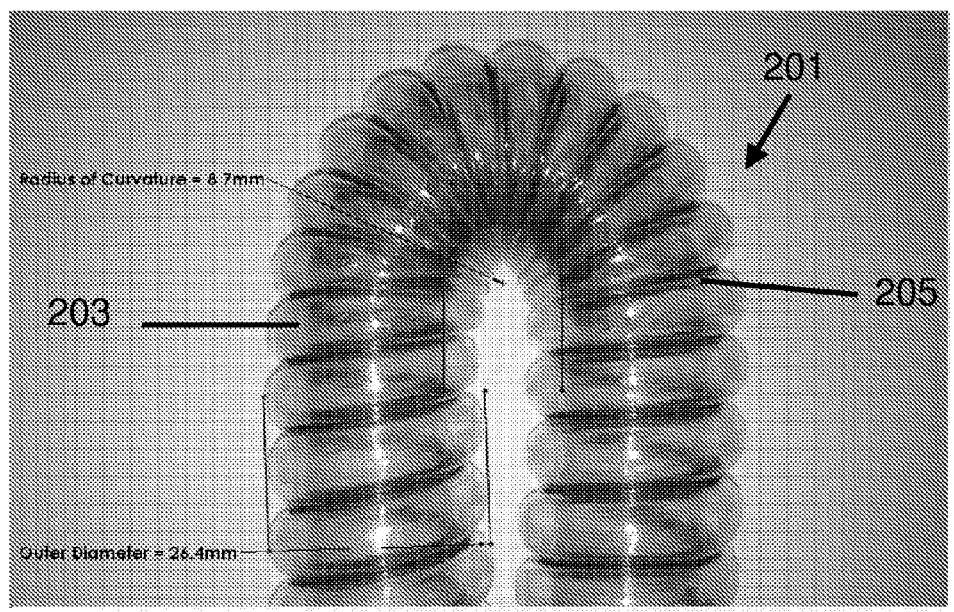
Figure 11C:
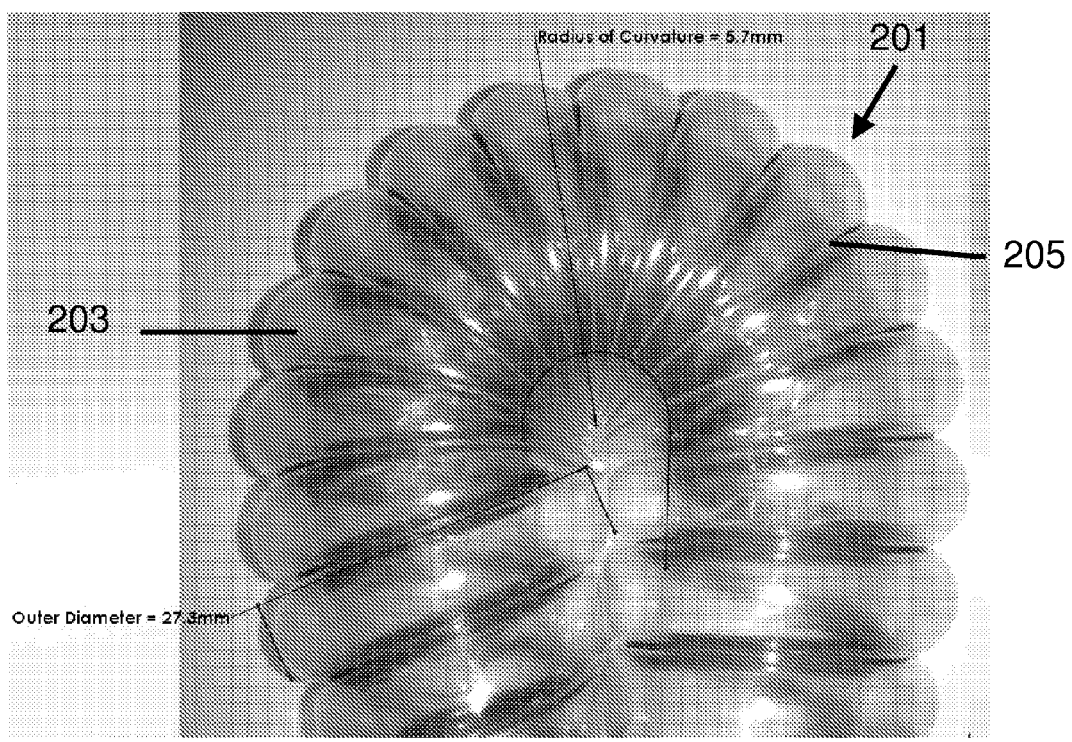

TABLE 7A shows the height of the bubble, the outer diameter and the radius of curvature of further configurations as shown in FIGS. 11A, 11B, and 11C.

TABLE 7A

|  | Tube (FIG.) | | |
| --- | --- | --- | --- |
|  | 11A | 11B | 11C |
| Bubble height (mm) | 6.6 | 8.4 | 9.3 |
| Outer diameter (mm) | 24.6 | 26.4 | 27.3 |
| Radius of curvature (mm) | 10 | 8.7 | 5.7 |

Figure 11D:
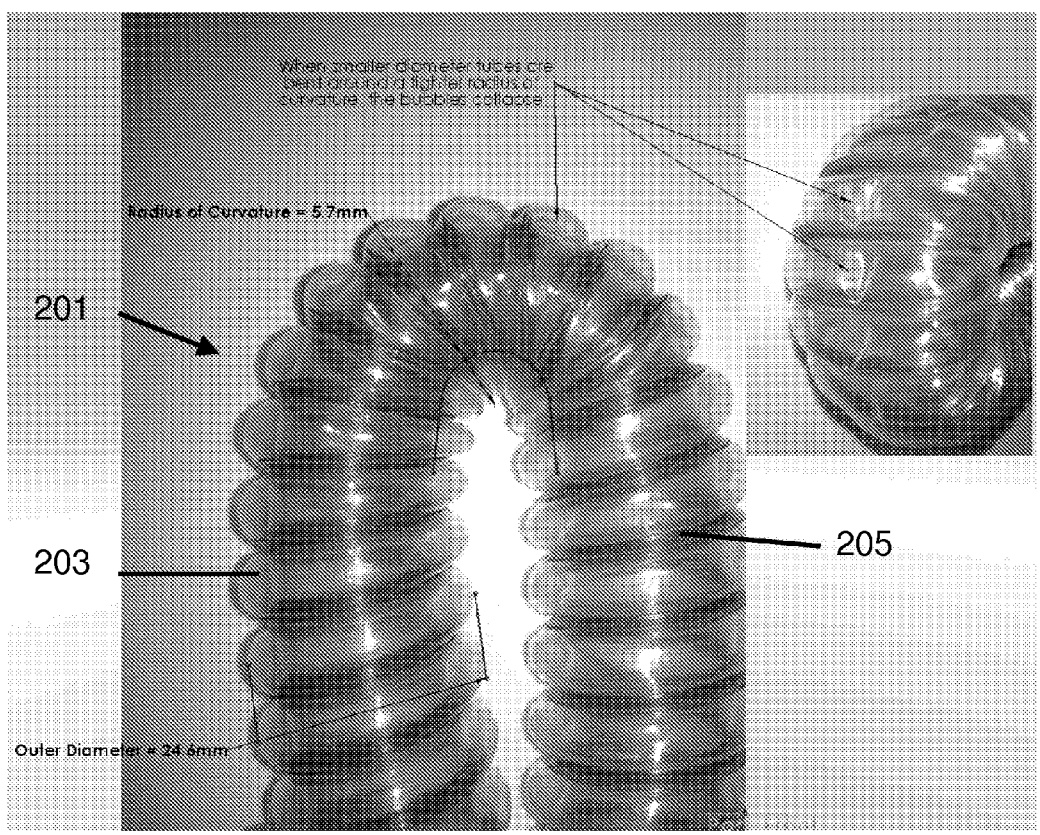

It should be noted that, in general, the smaller the radius of curvature, the tighter the tube can be bent around itself without the bubble collapsing or "kinking." For example, FIG. 11D shows a tube that has been bent beyond its radius of curvature (specifically, it shows the tube of FIG. 11A bent around a radius of curvature of 5.7 mm), thereby causing kinking in the walls of the bubble. Kinking is generally undesirable, as it can detract from the appearance of the tube, and can impair the thermal properties of the tube.

Accordingly, in some applications, configurations with increased bending properties (such as those shown in FIG. 9A or 9B) can be desirable despite having less efficient thermal properties. In some applications, it has been found that a tube with an outer diameter of 25 mm to 26 mm (or about 25 mm to about 25 mm) provides a good balance between thermal efficiency, flexibility, and bending performance. It should be appreciated that although the configurations of FIGS. 9A and 9B may be preferred in certain embodiments, other configurations, including those of FIGS. 11A-11D and other variations, may be utilized in other embodiments as may be desired.

Reference is next made to FIGS. 9C through 9F which demonstrate example positioning of heating element 215 with similar bubble shapes to improve thermal properties. The location of the heating element 215 can change the thermal properties within the composite tube 201.

FIG. 9C shows a longitudinal cross-section of a top portion of another composite tube. FIG. 9C shows an embodiment of a composite tube 201 where the heating elements 215 are centrally located in the second elongate member 205. This example shows the heating elements 215 close to one another and not close to the bubble wall.

Figure 9D:
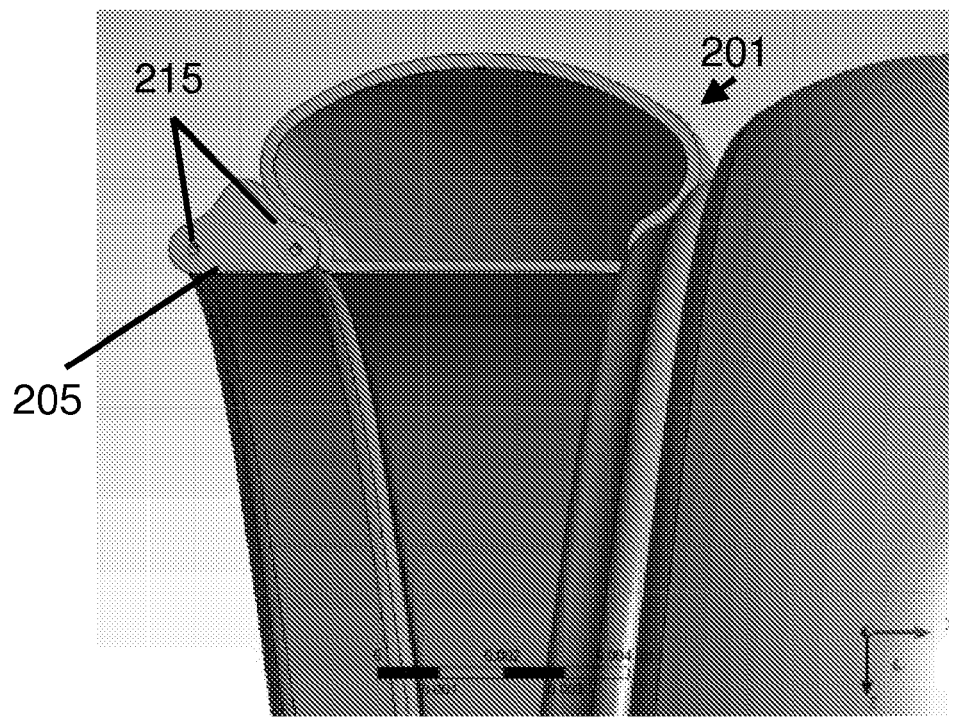
FIGS. 9D-F show examples of filament arrangements configured to improve thermal efficiency.

FIG. 9D shows a longitudinal cross-section of a top portion of another composite tube. FIG. 9D shows an embodiment of a composite tube 201 in which the heating elements 215 are spaced farther apart, as compared to FIG. 9C, in the second elongate member 205. These heating elements are closer to the bubble wall and provide for better regulation of heat within the composite tube 201.

Figure 9E:
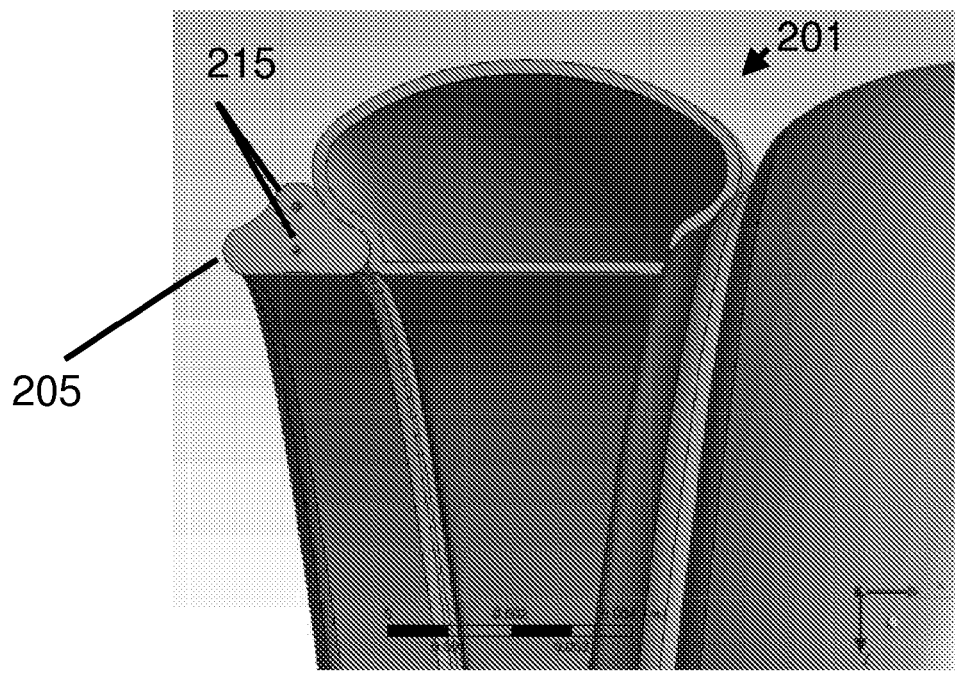

FIG. 9E shows a longitudinal cross-section of a top portion of another composite tube. FIG. 9E shows an embodiment of a composite tube 201 wherein the heating elements 215 are spaced on top of each other in the vertical axis of the second elongate member 205. In this example, the heating elements 215 are equally close to each bubble wall.

Figure 9F:
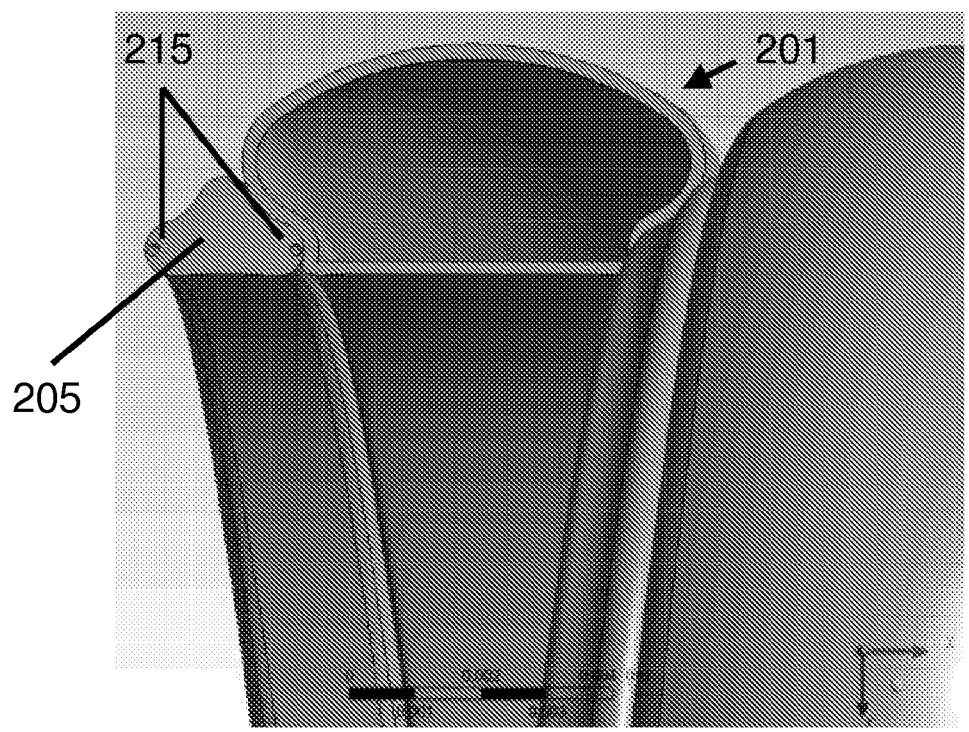

FIG. 9F shows a longitudinal cross-section of a top portion of another composite tube. FIG. 9F shows an embodiment of a composite tube 201 where the heating elements 215 are spaced at opposite ends of the second elongate member 205. The heating elements 215 are close to the bubble wall, especially as compared to FIGS. 9C-9E.

Of the four filament arrangements of FIGS. 9C-9F, FIG. 9F was determined to have the best thermal properties. Because of their similar bubble shapes, all of the configurations experienced similar heat loss from the tube. However, when the same thermal energy was input to the tubes, the filament configuration of FIG. 9F allowed for the largest temperature rise along the length of the tube. The configuration of FIG. 9D was determined to have the next best thermal properties and allowed for the next largest temperature rise along the length of tube. The configuration of FIG. 9C performed next best. The configuration of FIG. 9E had the poorest performance and allowed for the smallest temperature rise along the length of the tube, when the same amount of heat was input.

It should be appreciated that although the FIG. 9F configuration may be preferred in certain embodiments, other configurations, including those of FIGS. 9C, 9D, 9E, and other variations, may be utilized in other embodiments as may be desired.

Figure 10A:
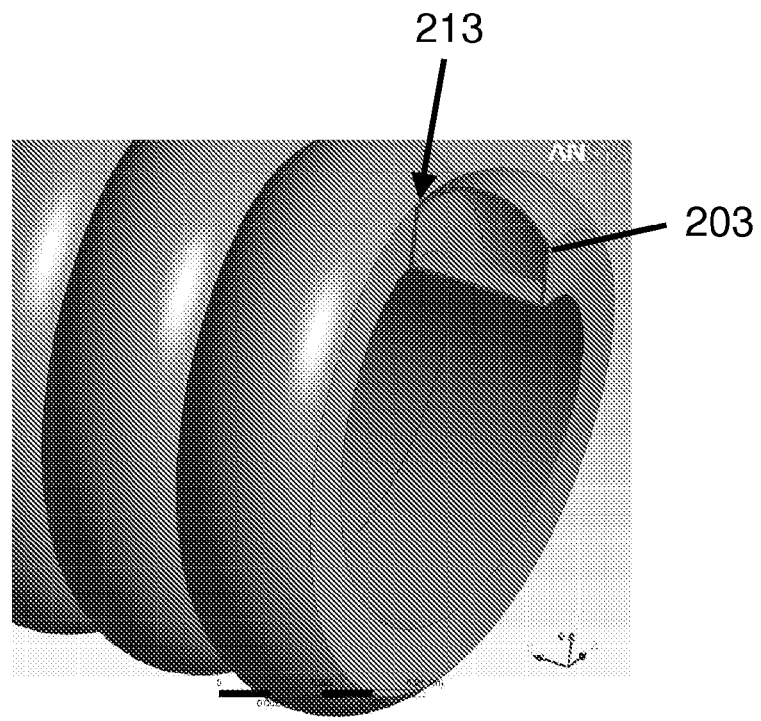
FIGS. 10A-C show examples of first elongate member stacking.
Figure 10B:
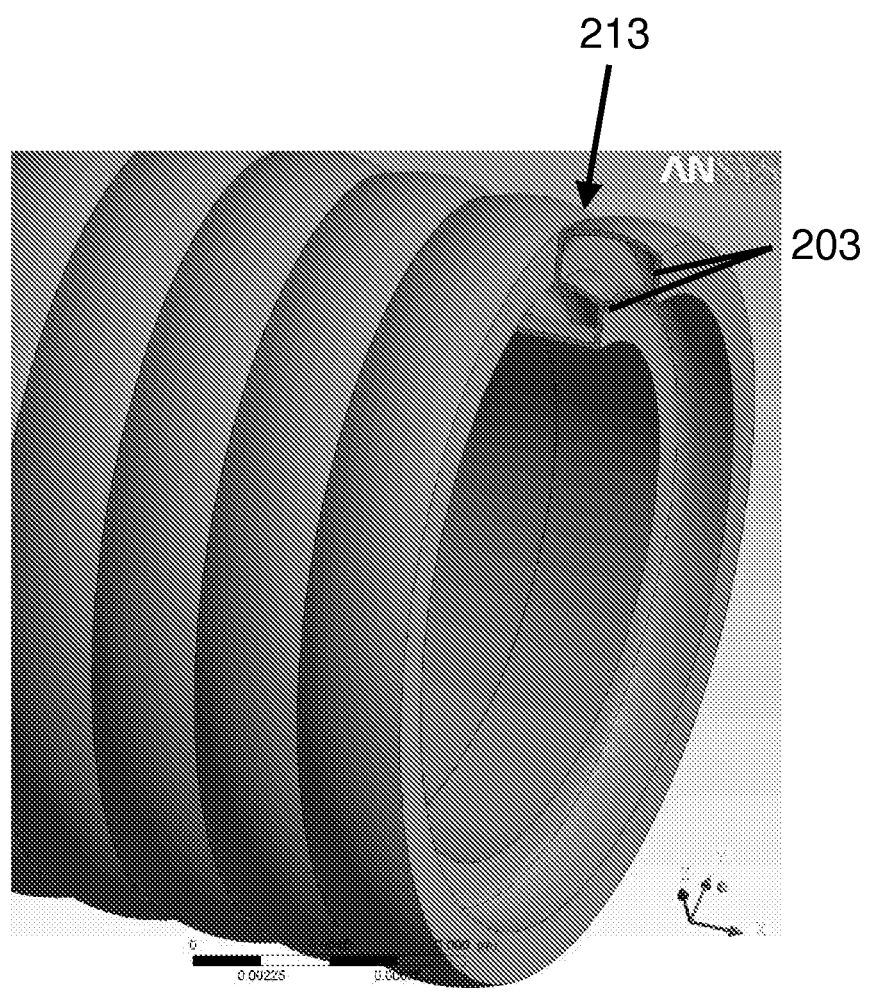
Figure 10C:
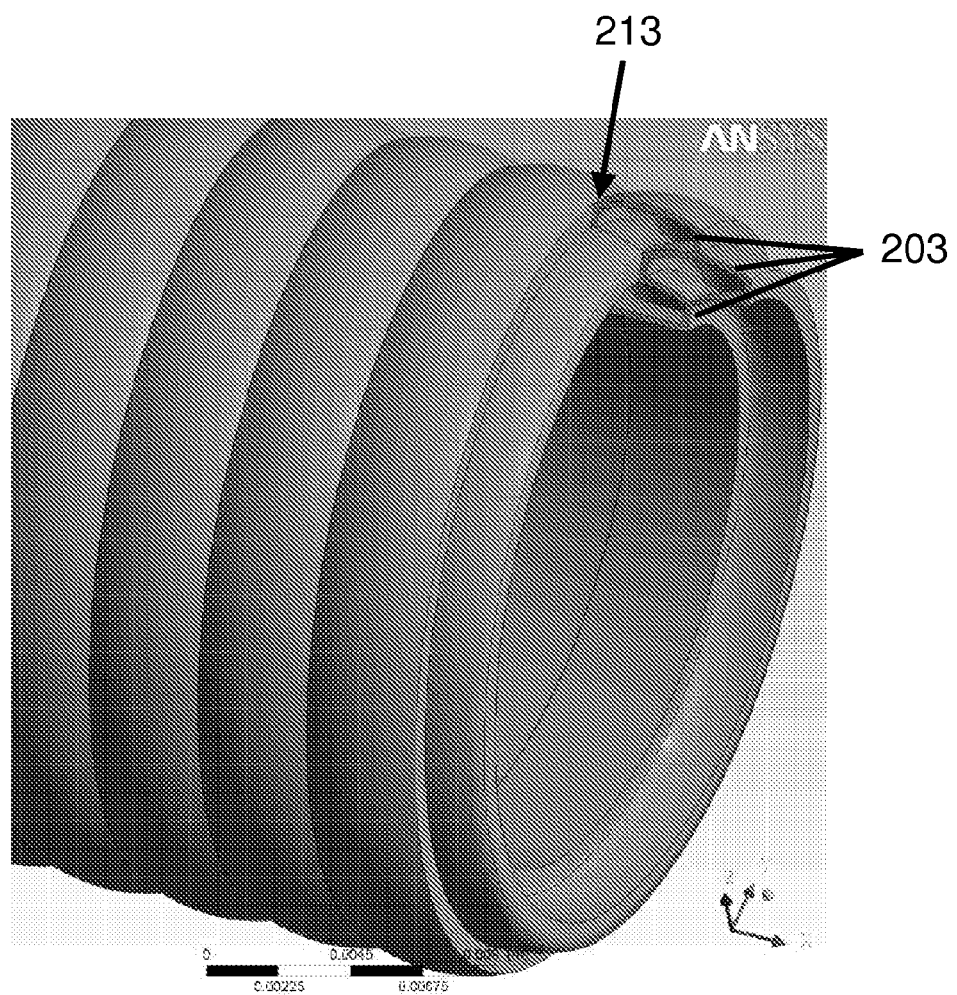

Reference is next made to FIGS. 10A through 10C, which demonstrate example configurations for stacking of the first elongate member 203. It was discovered that heat distribution can be improved in certain embodiments by stacking multiple bubbles. These embodiments can be more beneficial when using an internal heating filament 215. FIG. 10A shows a longitudinal cross-section of a top portion of another composite tube. FIG. 10A shows a cross section of a composite tube 201 without any stacking.

FIG. 10B shows a longitudinal cross-section of a top portion of another composite tube. FIG. 10B shows another example composite tube 201 with stacked bubbles. In this example, two bubbles are stacked on top of each other to form the first elongate member 203. As compared to FIG. 10A, the total bubble height is maintained, but the bubble pitch is half of FIG. 10A. Also, the embodiment in FIG. 10B has only a slight reduction in air volume. The stacking of the bubbles reduces natural convection and heat transfer in the gap between bubbles 213 and lowers the overall thermal resistance. The heat flow path increases in the stacked bubbles allowing heat to more easily distribute through the composite tube 201.

FIG. 10C shows a longitudinal cross-section of a top portion of another composite tube. FIG. 10C shows another example of a composite tube 201 with stacked bubbles. In this example, three bubbles are stacked on top of each other to form the first elongate member 203. As compared to FIG. 10A, the total bubble height is maintained, but the bubble pitch is a third of FIG. 10A. Also, the embodiment in FIG.

10B has only a slight reduction in air volume. The stacking of the bubbles reduces natural convection and heat transfer in the gap between bubbles 213.

Cleaning

In at least one embodiment, materials for a composite tube can be selected to handle various methods of cleaning. In some embodiments, high level disinfection (around 20 cleaning cycles) can be used to clean the composite tube 201. During high level disinfection, the composite tube 201 is subject to pasteurization at about 75° C. for about 30 minutes. Next, the composite tube 201 is bathed in 2% glutaraldehyde for about 20 minutes. The composite tube 201 is removed from the glutaraldehyde and submerged in 6% hydrogen peroxide for about 30 minutes. Finally, the composite tube 201 is removed from the hydrogen peroxide and bathed in 0.55% orthophthalaldehyde (OPA) for about 10 minutes.

In other embodiments, sterilization (around 20 cycles) can be used to clean the composite tube 201. First, the composite tube 201 is placed within autoclave steam at about 121° C. for about 30 minutes. Next, the temperature of the autoclave steam is increased to about 134° C. for about 3 minutes. After autoclaving, the composite tube 201 is surrounded by 100% ethylene oxide (ETO) gas. Finally, the composite tube 201 is removed from the ETO gas and submerged in about 2.5% glutaraldehyde for about 10 hours.

The composite tube 201 may be made of materials to withstand the repeated cleaning process. In some embodiments, part or all of the composite tube 201 can be made of, but is not limited to, styrene-ethylene-butene-styrene block thermo plastic elastomers, for example Kraiburg TF6STE. In other embodiments, the composite tube 201 can be made of, but is not limited to, hytrel, urethanes, or silicones.

The foregoing description of the invention includes preferred forms thereof. Modifications may be made thereto without departing from the scope of the invention. To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting.

What is claimed is:

1. A composite tube comprising:
   a first elongate member comprising a cross-sectional shape that defines a hollow body, wherein the first elongate member is spirally wound to form at least in part an elongate tube having a longitudinal axis, a lumen extending along the longitudinal axis, and a hollow wall defining a hollow space and at least partially surrounding the lumen; and
   a second elongate member spirally wound and joined between adjacent turns of the first elongate member, wherein surface portions of each of the first elongate member and the second elongate member form at least a portion of the lumen of the elongate tube, wherein the second elongate member acts as a structural support or reinforcement for the first elongate member.

2. The composite tube of claim 1 wherein the second elongate member is less flexible than the first elongate member.

3. The composite tube of claim 1 wherein the second elongate member provides crush resistance while being flexible enough to permit short-radius bends without kinking, occluding or collapsing.

4. The composite tube of claim 1 wherein portions of the first elongate member overlap adjacent turns of the second elongate member.

5. The composite tube of claim 1 wherein the second elongate member is solid or substantially solid.

6. The composite tube of claim 1 wherein the first elongate member forms in longitudinal cross-section a plurality of bubbles with a flattened surface at the lumen.

7. The composite tube of claim 6 wherein adjacent bubbles are separated by a gap above the second elongate member.

8. The composite tube of claim 7 wherein the gap permits shorter-radius bends.

9. The composite tube of claim 6 wherein the bubbles have perforations.

10. The composite tube of claim 1 wherein the second elongate member has a longitudinal cross-section that is wider proximal the lumen and narrower at a radial distance from the lumen.

11. The composite tube of claim 1 comprising one or more conductive filaments embedded or encapsulated in the second elongate member.

12. The composite tube of claim 11 wherein the second elongate member has a longitudinal cross-section that is generally triangular, generally T-shaped, or generally Y-shaped, and the one or more conductive filaments are embedded or encapsulated in the second elongate member on opposite sides of the triangle, T-shape, or Y-shape.

13. The composite tube of claim 1 wherein a part of the hollow wall at the lumen is thinner than a part of the hollow body opposed from the lumen.

14. The composite tube of claim 1 being one or more of: a medical circuit component, an inspiratory tube, an expiratory tube, a PAP component, an insufflation component, an exploratory component, and a surgical component.

15. A method of manufacturing a composite tube comprising:
   providing a first elongate member comprising a cross-sectional shape that forms a hollow body defining a hollow space and a second elongate member configured to provide structural support for the first elongate member;
   spirally wrapping the second elongate member around a mandrel with opposite side edge portions of the second elongate member being spaced apart on adjacent wraps, thereby forming a second-elongate-member spiral; and
   spirally wrapping the first elongate member that defines the hollow space around the second-elongate-member spiral, such that portions of the first elongate member overlap adjacent wraps of the second-elongate-member spiral and a portion of the first elongate member is disposed adjacent the mandrel in the space between the wraps of the second-elongate-member spiral, thereby forming a first-elongate-member spiral such that surface portions of each of the first elongate member and the second elongate member are located adjacent the mandrel.

16. The method of claim 15 comprising supplying air at a pressure greater than atmospheric pressure to an end of the first elongate member.

17. The method of claim 15 comprising cooling the second-elongate-member spiral and the first-elongate-member spiral to form a composite tube having a lumen extending along a longitudinal axis and a hollow space surrounding the lumen.

18. The method of claim 15 comprising forming the first and/or second elongate member.

19. The method of claim 18 wherein forming the first and/or second elongate members comprises extruding the first and/or second elongate members with a respective extruder.

20. The method of claim 18 wherein forming the second elongate member comprises embedding or encapsulating conductive filaments in the second elongate member.

21. A medical tube comprising:
an elongate hollow body spirally wound to form an elongate tube having a longitudinal axis, a lumen extending along the longitudinal axis, and a hollow wall defining a hollow space and at least partially surrounding the lumen, wherein the elongate hollow body has in transverse cross-section a wall defining at least a portion of the hollow wall, and wherein adjacent turns of the elongate hollow body do not overlap; and
a reinforcement portion, reinforcing the elongate hollow body, extending along a length of the elongate hollow body being spirally positioned between the adjacent turns of the elongate hollow body, wherein surface portions of each of the elongate hollow body and the reinforcement portion form a portion of the lumen of the elongate tube;
wherein the reinforcement portion is relatively thicker or more rigid than the wall defining at least a portion of the elongate hollow wall.

22. The medical tube of claim 21 wherein the reinforcement portion is formed from the same piece of material as the elongate hollow body.

23. The medical tube of claim 22 wherein the elongate hollow body in transverse cross-section comprises two reinforcement portions on opposite sides of the elongate hollow body.

24. The medical tube of claim 23 wherein opposite side edges of the reinforcement portions touch and/or overlap on adjacent turns of the elongate hollow body.

25. The medical tube of claim 21 wherein the reinforcement portion is formed from a separate piece of material than the elongate hollow body.

26. The medical tube of claim 21 wherein the hollow body forms in longitudinal cross-section a plurality of bubbles with a flattened surface at the lumen.

27. The medical tube of claim 26 wherein the bubbles have perforations.

28. The medical tube of claim 21 comprising one or more conductive filaments embedded or encapsulated within the reinforcement portion.

29. The medical tube of claim 21 being one or more of: a medical circuit component, an inspiratory tube, an expiratory tube, a PAP component, an insufflation component, an exploratory component, and a surgical component.

30. A method of manufacturing a medical tube comprising:
spirally winding an elongate hollow body around a mandrel without overlapping adjacent turns of the elongate hollow body to form an elongate tube having a longitudinal axis, a lumen extending along the longitudinal axis, and a hollow wall defining a hollow space and at least partially surrounding the lumen, wherein the elongate hollow body has in transverse cross-section a wall defining at least a portion of the hollow wall and two reinforcement portions on opposite sides of the elongate hollow body forming a portion of the lumen, the two reinforcement portions being relatively thicker or more rigid than the wall defining at least a portion of the hollow wall; and
joining adjacent reinforcement portions to each other such that opposite edges of the reinforcement portions touch on adjacent turns of the elongate hollow body and surface portions of each of the hollow wall and the reinforcement portions form at least a portion of the lumen.

31. The method of claim 30 wherein joining adjacent reinforcement portions to each other causes edges of the reinforcement portions to overlap.

32. The method of claim 30 comprising supplying air at a pressure greater than atmospheric pressure to an end of the elongate hollow body.

33. The method of claim 30 comprising cooling the elongate hollow body to join adjacent reinforcement portions to each other.

34. The method of claim 30 comprising extruding the elongate hollow body.

35. The method of claim 30 comprising embedding or encapsulating one or more conductive filaments in the reinforcement portions.

* * * * *